US008647820B2

(12) United States Patent  
Lee et al.

(10) Patent No.: US 8,647,820 B2
(45) Date of Patent: Feb. 11, 2014

(54) CIRCULAR DUMBBELL DECOY OLIGODEOXYNUCLEOTIDES (CDODN) CONTAINING DNA BINDINGS SITES OF TRANSCRIPTION

(75) Inventors: In-Kyu Lee, Taegu (KR); Ryuichi Morishita, Osaka (JP)

(73) Assignees: Anges MG, Inc., Osaka (JP); In-kyu Lee, Taegu (KR)

( * ) Notice: Subject to any disclaimer, the term of this patent is extended or adjusted under 35 U.S.C. 154(b) by 0 days.

(21) Appl. No.: 13/036,578

(22) Filed: Feb. 28, 2011

(65) Prior Publication Data

US 2011/0250261 A1 Oct. 13, 2011

Related U.S. Application Data

(62) Division of application No. 10/512,486, filed as application No. PCT/JP02/04303 on Apr. 26, 2002, now abandoned.

(51) Int. Cl.
*C12Q 1/68* (2006.01)
*C12P 19/34* (2006.01)
*C07H 21/02* (2006.01)
*C07H 21/04* (2006.01)
*A61K 38/00* (2006.01)

(52) U.S. Cl.
USPC ......... 435/6.1; 435/6.11; 435/91.1; 536/23.1; 536/24.3; 514/15.1

(58) Field of Classification Search
USPC ........... 435/6.1, 6.11, 91.1, 183; 436/94, 501; 536/23.1, 24.3, 24.33, 25.3; 514/15.1
See application file for complete search history.

(56) References Cited

FOREIGN PATENT DOCUMENTS

| EP | 0824918 | 2/1998 |
|---|---|---|
| JP | 2005523703 | 8/2005 |
| WO | WO9511687 | 5/1995 |

OTHER PUBLICATIONS

The definition of "encyclopedia". Printed on Nov. 9, 2012.*
Chu et al., "Crosslinking transcription factors to their recognition sequences with Pt$^{II}$ complexes," Nucleic Acid Research, 20(10): 2497-2502 (1992).
Chu et al., "Binding of hairpin and dumbbell DNA to transcription factors," Nucleic Acids Research, 19(24):6958 (1991).
"Route of administration" from Wikipedia, the free encyclopedia, printed on Dec. 21, 2010.
Abe et al., "Specific inhibition of influenza virus RNA polymerase and nucleoprotein gene expression by circular dumbbell RNA/DNA chimeric oligonucleotides containing antisense phosphodiester oligonucleotides," FEBS Letters, 425(1):91-96 (1998).
ACS: Clinical Trials: What You Need to Know, printed on May 9, 2009.
Adderley et al., "Oxidative damage of cardiomyocytes is limited by extracellular regulated kinases ½-mediated induction of cyclooxygenase-2," The Journal of Biological Chemistry, 274(8):5038-5046 (1999).
Ahn et al, "Inhibitory Effects of Novel AP-1 Decoy Oligodeoxynucleotides on Vascular Smooth Muscle Cell Proliferation In Vitro and Neointimal Formation In Vivo," Circulation Research, 90(12): 1325-1332 (2002).
Ahn et al., "Transcription factor decoy for activator protein-1 (AP-1) inhibits high glucose- and angiotensin II-induced type 1 plasminogen activator inhibitor (PAI-1) gene expression in cultured human vascular smooth muscle cells," Diabetologia, 44:713-720 (2001).
Akimoto et al., "Growth inhibition of cultured human tenon's fibroblastic cells by targeting the E2F transcription factor," Experimental Eye Research, 67(4):395-401 (1998).
Alkalay et al., "In vivo stimulation of I kappa B phosphorylation is not sufficient to activate NF-kappa B," Molecular and Cellular Biology, 5(3):1294-301 (1995).
Alper et al., "Apoptosis, growth arrest and suppression of invasiveness by CRE-decoy oligonucleotide in ovarian cancer cells: Protein kinase A downregulation and cytoplasmic export of CRE-binding proteins," Molecular and Cellular Biochemistry, 218:55-63 (2001).
Aoki et al., "Gene therapy for arteriosclerotic diseases," Nippon Rinsho, 59(1):43-52 (2001) (English-language abstract).
Ashida et al., "Ap-1 and colorectal cancer," Inflammopharmacology, 1(1-3): 113-125 (2005).
Bennett et al., "Inhibition of vascular smooth muscle cell proliferation in vitro and in vivo by C-myc antisense oligodeoxynucleotides," Journal of Clinical Investigation., 93:820-828 (1994).
Berkowitz et al., "Multiple sequence elements of a single functional class are required for cyclic AMP responsiveness of the mouse c-fos promoter," Molecular and Cellular Biology, 9(10):4272-4281 (1989).
Bielinska et al., "Regulation of gene expression with double-stranded phosphorothioate oligonucleotides," Science, 250(4983):997-1000 (1990).
Briata et al., "c-myc Gene expression in human cells is controlled by glucose," Biochemical and Biophysical Research Communications, 165(3):1123-1129 (1989).
Brown et al., "Effect of phosphorothioate modification of oligodeoxynucleotides on specific protein binding," The Journal of Biological Chemistry, 269(43):26801-26805 (1994).
Brunner et al, "Single bilayer vesicles prepared without Sonication Physico-clemical properties," Biochimica et Biophysica Acta Biomembranes, 455(2):322-331 (1976).

(Continued)

*Primary Examiner* — Frank Lu
(74) *Attorney, Agent, or Firm* — Ropes & Gray LLP; James F. Haley, Jr.; Brian M. Gummow

(57) ABSTRACT

The present invention provides a circular dumbbell oligodeoxynucleotide (CDODN) comprising two loop structures and a stem structure, wherein the stem structure comprises a nucleotide sequence capable of binding the DNA-binding domain of a transcriptional factor. The present invention further provides a pharmaceutical composition comprising said CDODN. The pharmaceutical composition can be used for treating and/or preventing a disease or disorder related to such a transcriptional factor. The present invention also provides a method for treating and/or preventing a disease or disorder related to such a transcriptional factor, comprising administering to the subject a therapeutically effective amount of a CDODN comprising two loop structures and a stem structure, wherein the stem structure comprises a nucleotide sequence capable of binding the DNA-binding domain of the transcriptional factor.

4 Claims, 14 Drawing Sheets

(56) References Cited

OTHER PUBLICATIONS

Buchwald et al., "Decoy oligodeoxynucleotide against activator protein-1 reduces neointimal proliferation after coronary angioplasty in hypercholesterolemic minipigs," Journal of the American College of Cardiology, 39(4):732-738 (2002).
Burgess et al., "The antiproliferative activity of c-myb and c-myc antisense oligonucleotides in smooth muscle cells is caused by a nonantisense mechanism," Proceedings of the National Academy of Sciences of the United States of America, 92:4051-4055 (1995).
Cattaruzza et al., "Mechanosensitive transcription factors involved in endothelin B receptor expression," The Journal of Biological Chemistry, 276(40):36999-37003 (2001).
Cereghini et al., "A liver-specific factor essential for albumin transcription differs between differentiated and dedifferentiated rat hepatoma cells," Genes and Development, 2(8):957-974 (1988).
Cho-Chung et al., "CRE-decoy oligonucleotide-inhibition of gene expression and tumor growth," Molecular and Cellular Biochemistry, 212:29-34 (2000).
Chu et al., "The stability of different forms of double-stranded decoy DNA in serum and nuclear extracts," Nucleic Acids Research, 20(21):5857-5858 (1992.
Clowes et al., "Mechanisms of stenosis after arterial injury," Laboratory Investigation, 49(2):208-215 (1983).
Clusel et al., "Ex vivo regulation of specific gene expression by nanomolar concentration of double-stranded dumbbell oligonucleotides," Nucleic Acids Research, 21(15):3405-3411 (1993).
Corpet, "Multiple sequence alignment with hierarchical clustering," Nucleic Acids Research, 16(22):10881-10890 (1988).
Currier et al., "Restenosis after percutaneous transluminal coronary angioplasty: have we been aiming at the wrong target?," Journal of the American College of Cardiology, 25(2):516-520 (1995).
Davis, "The mitogen-activated protein kinase signal transduction pathway," The Journal of Biological Chemistry, 268(20):14553-14556 (1993).
Deamer, "Preparation and properties of ether-injection liposomes," Annals of the New York Academy of Sciences, 308:250-258 (1978).
Di Paolo et al., "High glucose concentration induces the overexpression of transforming growth factor-β through the activation of a platelet-derived growth factor loop in human mesangial cells," American Journal of Pathology, 149(6):2095-2106(1996).
Ehsan et al., "Long-term stabilization of vein graft wall architecture and prolonged resistance to experimental atherosclerosis after E2F decoy oligonucleotide gene therapy," The Journal of Thoracic and Cardiovascular Surgery, 121(4):714-722 (2001).
Feng et al,, "The interleukin-4/interleukin-13 receptor of human synovial fibroblasts: overexpression of the nonsignalling interleukin-13 receptor α2," Laboratory Investigation, 78(5):591-601 (1998).
Gao et al., "Phosphorothioate oligonucleotides are inhibitors of kuman DNA polymerases and Rnase H: implications for antisense technology," Molecular Pharmacology, 41(2):223-229 (1992).
Gura, Systems for identifying new drugs are often faulty, Science, 278, 1041 and 1042, 1997.
Higgins et al., "Clustal: a package for performing multiple sequence alignment on a microcomputer," Gene, 73(1):237-244 (1988).
Higgins et al., "Fast and sensitive multiple sequence alignments on a microcomputer," Computer Applications in the Biosciences, 5(2):151-153 (1989).
Hosoya et al., "Sequence-specific inhibition of a transcription factor by circular dumbbell DNA oligonucleotides," FEBS Letters, 461:136-140 (1999).
Hu et al., "Activation of mitogen-activated protein kinases (ERK/JNK) and AP-1 transcription factor in rat carotid arteries after balloon injury," Arteriosclerosis, Thrombosis, and Vascular Biology, 17(11):2808-2816 (1997).
Huang et al., "Parallelization of a local similarity algorithm," Computer Applications in the Biosciences, 8(2):155-165 (1992).
Inaba et al., "Enhanced expression of platelet-derived growth factor-βreceptor by high glucose," Diabetes, 45:507-512 (1996).
Izumi et al., "Gene transfer of dominant-negative mutants of extracellular signal-regulated kinase and c-Jun NH2-terminal kinase prevents neointimal formation in balloon-injured rat artery," Circulation Research, 88:1120-1126, (2001).
Jin et al., "Regulation of clusterin gene expression by transforming growth factor β," The Journal of Biological Chemistry, 272(42):26620-26626 (1997).
Kaneda et al., "Development of in vivo gene transfer methods towards future gene therapy," J. Clin. Pathol., 45(2):99-105 (1997) (English-language abstract).
Kaneda et al., "Gene therapy for reperfusion injury via endothelial protection and control of adhesion molecule due to control of transcription regulation Factor NEκB," Rinsho Seijin byo, 31(1):1399-1400 (2001) (English translation attached).
Kanekiyo et al., "Zinc-induced activation of the human cytomegalovirus major immediate-early promoter is mediated by metallothionein and nuclear factor-κB," Toxicology and Applied Pharmacology, 173:146-153 (2001).
Karin, "The regulation of AP-1 activity by mitogen-activated protein kinases," The Journal of Biological Chemistry, 270(28):16483-16486 (1995).
Kawamura et al., "Intratumoral injection of oligonucleotides to the NfκB binding site inhibits cachexia in a mouse tumor model," Gene Therapy, 6:91-97 (1999).
Kawauchi et al., "Downregulation of nuclear factor kappa B expression in primate cardiac allograft arteries after E2F decoy transfection," Transplantation Proceedings, 33:451 (2001).
Kawauchi et al., "Gene therapy for attenuating cardiac allograft arteriopathy using ex vivo E2F decoy transfection by HVJ-AVE-liposome method in mice and nonhuman primates," Circulation Research, 87(11):1063-1068 (2000).
Khaled et al., "Multiple mechanisms may contribute to the cellular anti-adhesive effects of phosphorothioate oligodeoxynucleotides," Nucleic Acids Research, 24(4):737-745 (1996).
Khaled et al., "Use of Phosphorothioate-modified oligodeoxynucleotides to inhibit NF-κB expression and lymphocyte function," Clinical Immunology and Immunopathology. 86(2):170-179 (1998).
Kodama et al., "The Features and Shortcomings for Gene Delivery of Current Non-Viral Carriers," Current Medicinal Chemistry, 13:2155-2161 (2006).
Koyama et al., "Cell replication in the arterial wall: activation of signaling pathway following in vivo injury," Circulation Research, 82:713-721 (1998).
Larrouy et al., "RNase H-mediated inhibition of translation by antisense oligodeoxyribo-nucleotides: use of backbone modification to improve specificity," Gene, 121:189-194 (1992).
Lauth et al., "Transcriptional control of deformation-induced preproendothelin-1 gene expression in endothelial cells," The Journal of Molecular Medicine, 78:441-450 (2000).
Lee et al., "Advantages of the Circular Dumbbell Decoy in Gene Therapy and Studies of Gene Regulation," Current Drug Targets, 4:619-623 (2003).
Lee et al., "Transcription factor decoy ODN for activator protein-1 (AP-1) inhibits expression of type 1 plasminogen activator inhibitor (PAI-1) gene induced by high glucose and angiotensin II in cultured human vascular smooth muscle cells," Diabetes, 50(2) (2001). (Abstract of 61st Scientific Sessions of the American Diabetes Association XP009001233).
Le-Niculescu et al., "Withdrawal of survival factors results in activation of the JNK pathway in neuronal cells leading to Fas ligand induction and cell death," Molecular and Cellular Biology, 19(1):751-763 (1999).
Lim et al., "Sequence-independent inhibition of RNA transcription by DNA dumbbells and other decoys," Nucleic Acids Research, 25:575-581 (1997).
Lim et al., "Sequence-independent inhibition of RNA transcription by DNA dumbbells and other decoys," Nucleic Acids Research, 25(3):575-581 (1997).
Lindner et at., "Role of basic fibroblast growth factor in vascular lesion formation," Circulation Research, 68:106-113 (1991).
Liu et al., "Restenosis after coronary angioplasty," Circulation, 79(6):1374-1387 (1989).

(56) References Cited

OTHER PUBLICATIONS

Maeshima et al., "Inhibition of mesangial cell proliferation by E2F decoy oligodeoxynucleotide in vitro and in vivo," The Journal of Clinical Investigation, 101(11):2589-2597 (1998).
Mangi et al., "Gene therapy for human bypass grafts," Annals of Medicine, 33:153-155 (2001).
Mann et al., "Ex-vivo gene therapy of human vascular bypass grafts with E2F decoy: the PREVENT single-centre, randomised, controlled trial," The Lancet, 354:1493-1498 (1999).
Mann et al., "Therapeutic applications of transcription factor decoy oligonucleotides," The Journal of Clinical Investigation, 106(9): 1071-1075 (2000).
Marcus-Sekura et al., "Techniques for using antisense oligodeoxyribonucleotides to study gene expression," Analytical Biochemistry, 172:289-295 (1988).
Mastrobattista et al, "Delivery of Nucleic Acids," Pharmaceutical Research, 24(8):1561-1563 (2007).
McCarthy, "Early and aggressive treatment saves US anthrax victims," The Lancet, 358:1703 (2001).
Miano et al., "Smooth muscle cell immediate-early gene and growth factor activation follows vascular injury," Arteriosclerosis and Thrombosis, 13(2):211-219 (1993).
Moon et al., "Potent growth inhibition of leukemic cells by novel ribbon-type antisense oligonucleotides to c-mybl," The Journal of Biological Chemistry, 275(7):4647-4653 (2000).
Morishita et al., "A gene therapy strategy using a transcription factor decoy of the E2F binding site inhibits smooth muscle proliferation in vivo," PNAS, 92:5855-5859 (1995).
Morismta et al,, "Gene therapy in vascular medicine: recent advances and future perspectives," Pharmacology & Therapeutics, 91:105-114 (2001).
Morishita et al., "In vivo transfection of cis element "decoy" against nuclear factor-κB binding site prevents myocardial infarction," Nature Medicine, 3(8):894-899 (1997).
Morishita et al., "Intimal hyperplasia after vascular injury is inhibited by antisense cdk 2 kinase oligonucleotides," tThe Journal of Clinical Investigation, 93:1458-1464 (1994).
Morishita et al, "Role of AP-1 complex in angiotensin II-mediated transforming growth factor-β expression and gowth of smooth muscle cells:.using decoy approach against AP-1 binding site," Biochemical and Biophysical Research Communications, 243:361-367 (1998).
Morishita et al., "Single intraluminal delivery of antisense cdc2 kinase and proliferating-cell nuclear antigen oligonucleotides results in chronic inhibition of neointimal hyperplasia," Proceedings of the National Academy of Sciences of the United States of America, 90:8474-8478 (1993).
Muller et al., "Experimental models of coronary artery restenosis," Journal of the American College of Cardiology, 19:418-432 (1992).
Myers et al., "Optimal alignments in linear space," Computer Applications in the Biosciences, 4(1):11-17 (1988).
Naka et al., "Animal Models and Novel Insights Into the Vascular Complications of Diabetes, Arteriosclerosis," Thrombosis and Vascular Biology, 24:1342-1349 (2004).
Natarajan et al., "Angiotensin II signaling in vascular smooth muscle cells under high glucose conditions," Hypertension, 33:378-384 (1999).
Needleman et al., "A general method applicable to the search for similarities in the amino acid sequence of two proteins," Journal of Molecular Biology, 48:443-453 (1970).
Nishikawa et al., "Nonvirai Vectors in the New Millennium: Delivery Barriers in Gene Transfer," Human Gene Therapy, 12:861-870 (2001).
Ohashi et al., "Role of p38 mitogen-activated protein kinase in neointimal hyperplasia after vascular injury," Arteriosclerosis, Thrombosis and Vascular Biology, 20(12):2521-2526 (2000).
Pagano et al., "Association of cdk2 kinase with the transcription factor E2F during S phase," Science, 255 (5048)1144-1147 (1992).
Pagano et al., "Cyclin A is required at two points in the human cell cycle," The EMBO Journal, 11 (3):961-971 (1992).
Pardee, "A restriction point for control of normal animal cell proliferation," Proceedings of the National Academy of Sciences of the United States of America. 71(4):1286-1290 (1974).
Park et al., "Inhibition of HIV-1 Replication by a New Type of Circular Dumbbell RNA/DNA Chimeric Oligonucleotides." Biochemical and Biophysical Research Communications, 270(3):953-960 (2000).
Park et al.. "Dual blockade of cyclic AMP response element- (CRE) and AP-1-directed transcription by CRE-transcription factor decoy oligonucleotide," The Journal of Biological Chemistry. 274(3):1573-1580 (1999).
Parry et al., "A set of inducible genes expressed by activated human monocytic and endothelial cells contain κB-like sites that specifically bind c-Rel-p65 heterodimers," The Journal of Biological Chemistry, 269(33):20823-20825 (1994).
Pauletto et al., "Smooth-muscle-cell proliferation and differentiation in neointima formation and vascular restenosis," Clinical Science, 87(5):467-479 (1994).
Pearson et al., "Improved tools for biological sequence comparison," Proceedings of the National Academy of Sciences of the United States of America, 85:2444-2448 (1988).
Pearson, "Using the FASTA program to search protein and DNA sequence databases," Methods in Molecular Biology, 24:307-331 (1994).
Perel et al., "Comparison of treatment effects between animal experiments and clinical trials: Systematic review," British Medical Journal, 334:197 (2006).
Pyles et al, "Activation of MAP kinases in vivo follows balloon overstretch injury of porcine coronary and carotid arteries," Circulation Research, 81:904-910 (1997).
Romanelli et al "Molecular Interaction Between Nuclear Factor κB (NF-κB) Transcription Factors and a PNA-DNA Chimera Mimicking NF—κB Binding Sites," European Journal of Biochemistry, 268:6066-6075 (2001).
Rosenblatt et al., "Human cyclin-dependent kinase 2 is activated during the S and G2 phases of the cell cycle and associates with cyclin A," PNAS, 89:2824-2828 (1992).
Ross, "The pathogenesis of atherosclerosis: a perspective for the 1990s," Nature, 362:801-808 (1993).
Sawa et al., "A novel strategy for myocardial protection using in vivo transfection of cis element 'decoy' against NFκB binding site," Circulation, 96(9)II-280-II-285 (1997).
Schöler et al., "Specific interaction between enhancer-containing molecules and cellular components," Cell, 36(2):403-411 (1984).
Schwartz et al., "The intima," Circulation Research, 77:445-465 (1995).
Seger et al., "The MAPK Signaling Cascade," The FASEB Journal, 9(9):726-735 (1995).
Simons et at, "Antisense proliferating cell nuclear antigen oligonucleotides inhibit intimal hyperplasia in a rat carotid artery injury model," Clinical Investigation, 93:2351-2356 (1994).
Simons et al., "Antisense c-myb oligonucleotides inhibit intimal arterial smooth muscle cell accumulation in vivo," Nature, 359:67-70 (1992).
Smith, "Comparison of biosequences," Advances in Applied Mathematics, 2(4):482-489 (1981).
Stein et al., "Otigodeoxynucleotides as inhibitors of gene expression: a review," Cancer Research, 48(10):2659-2668 (1988).
Subraramaiah et at., "Peroxisome proliferator-activited receptor γ ligands suppress the transcriptional activation of cyclooxygenase-2," The Journal of Biological Chemistry, 276(15):12440-12448 (2001).
Suzuki et al., "E2F decoy suppresses E-selectin expression in murine cardiac allograft arteriophathy," Transplantation Proceedings, 31:2018-2019 (1999).
Szoka et al., "Preparation of unilamellar liposomes of intermediate size (0.1-.0.2. μm) by a combination of reverse phase evaporation and extrusion through polycarbonate membranes," Biochimica et Biophysica Acta Biomembranes, 601(3):559-571 (1980).
Taimor et al, "Transcription activator protein 1(AP-1) mediates NO-induced apoptosis of adult cardiomyocytes," The FASEB Journal, 15:2518-2520 (2001) (online document included).

(56) References Cited

OTHER PUBLICATIONS

Tanaka et al., "Sequence-specific interaction of α-β-anomeric double-stranded DNA with the p50 subunit of NFκB: application to the decoy approach," Nucleic Acids Research, 22(15):3069-3074 (1994).

Tomita et al., "An oligonucleotide decoy for transcription factor E2F inhibits mesangial cell proliferation in vitro," the American Physiological Society, 275:F278-F284 (1998).

Viedt et al., "The terminal complement complex C5b-9 stimulates interleukin-6 production in human smooth muscle cells through activation of transcription factors NF-κB and AP-1," The FASEB Journal, 14:2370-2372 (2000).

Von Knethen et al., "NF-κB and AP-1 activation by nitric oxide attenuated apoptotic cell death in RAW 264.7 macrophages," Molecular Biology of the Cell, 10:361-372 (1999).

Von Knethen et al., "Superoxide attenuates macrophage apoptosis by NF-κB and AP-1 activation that promotes cyclooxygenase-2 expression," The Journal of Immunology, 163(5):2858-2866 (1999).

Wagner et al., "Decoy oligodeoxunucletide characterization of transcription factors controlling endothelin-B receptor expression in vascular smooth muscle cells," Molecular Pharmacology, 58(6):1333-1340 (2000).

Weintraub et al., "Retinoblastoma protein switches the E2F site from positive to negative element," Nature, 358:259-261 (1992).

White et al., "What in vitro models of infection can and cannot do," Pharmacotherapy, 21: 292S-301S (2001).

Whitmarsh et al., "Transcription factor AP-1 regulation by mitogen-activated protein kinase signal transduction pathways," Journal of Molecular Medicine, 74(10):589-607 (1996).

Yamamoto et al., "Decoy Oligonucleotides," Cellular Molecular Medicine, 1(3):78-79 (2000) (English translation attached).

Yasunari et al., "Mechanisms of action of troglitazone in the prevention of high glucose-induced migration and proliferation of cultured coronary smooth muscle cells," Circulation Research, 81:953 (1997).

Yoshida et al., "Suppression of proliefrative cholangitis by E2F decoy oligodeoxynucleotide," Journal of Surgical Research, 102:95-101 (2002).

Yoshida et al., "Suppression of proliferative cholangitis by E2F decoy oligodeoxynucleotide," Journal of Surgical Research, 102:95-101 (2002).

Yoshizumi et al., "Down-regulation of the cyclin a promoter by transforming growth factor-β1 is associated with a reduction in phosphorylated activating transcription factor-1 and cyclic AMP-responsive element-binding protein," The Journal of Biological Chemistry, 272(35):22259-22264 (1997).

\* cited by examiner

FIG. 3
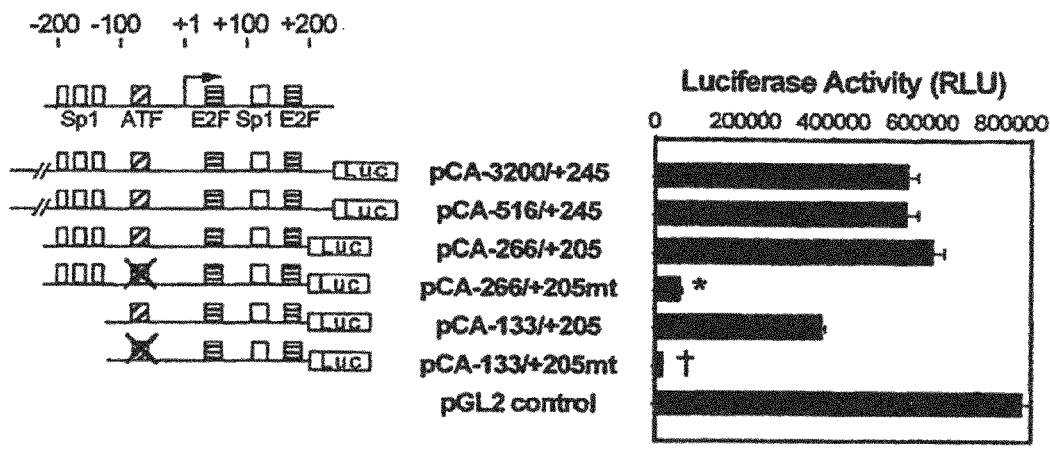
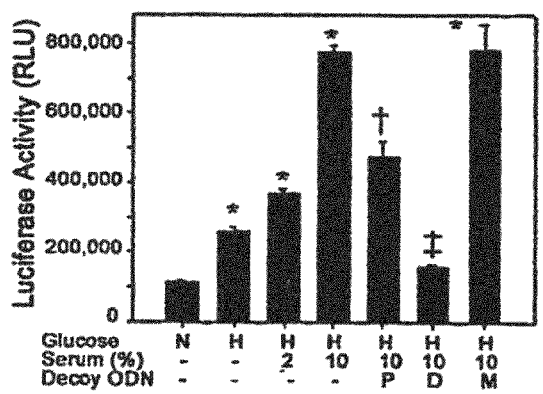
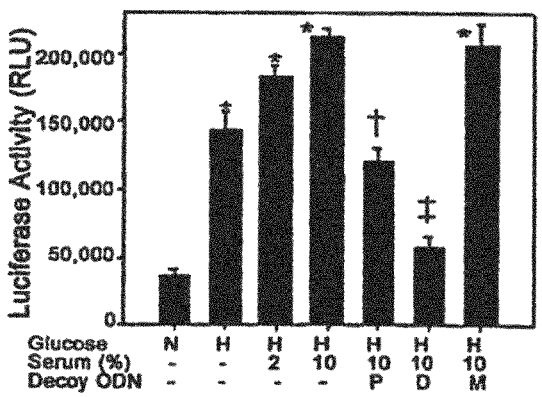
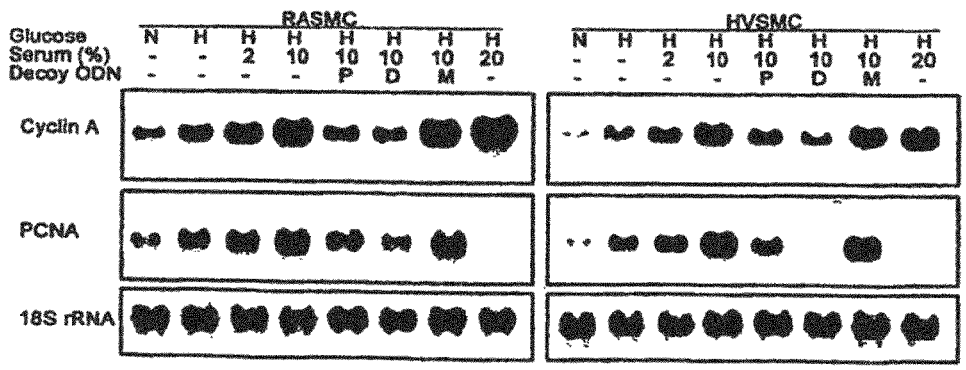

FIG. 4
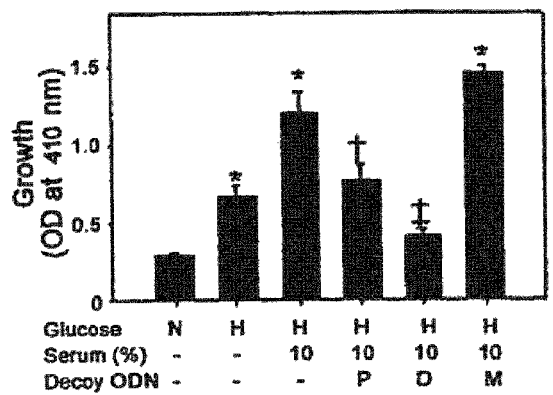
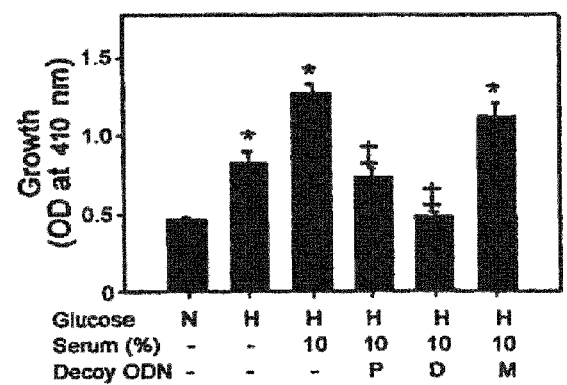
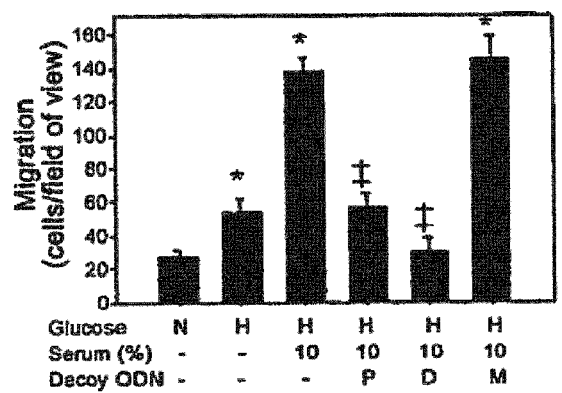
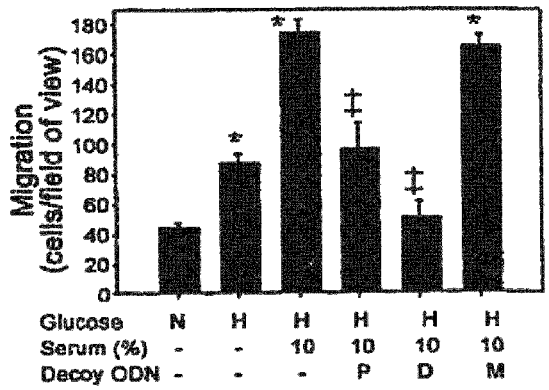

PSODN
5'-ATsTTAAGTTTCGCGCCCTTTCTCAsAs-3'
3'-sTsAAATTCAAAGCGCGGGAAAGAGsTT-5'

Anealed
form
```
      A  A GCAATAGCGCGAAAC
      A  A CGTTATCGCGCTTTGCCTAGG-p
```

CDODN
```
   A  A GCAATAGCGCGAAACGGATCCGTTTCGCGCTATTGC A  A
   A  A CGTTATCGCGCTTTGCCTAGGCAAAGCGCGATAACG A  A
```

MODN
```
   A  A GCAATAAATCGAAACGGATCCGTTTCGATTTATTGC A  A
   A  A CGTTATTTAGCTTTGCCTAGGCAAAGCTAAATAACG A  A
```

B

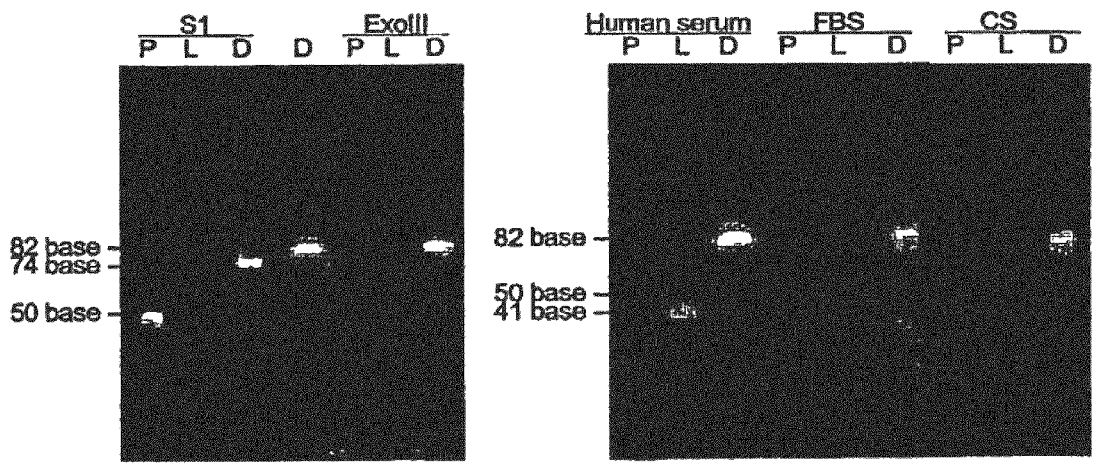

FIG. 9
A
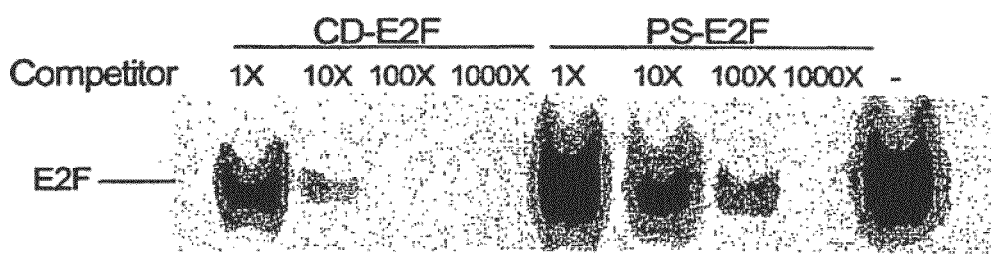
B
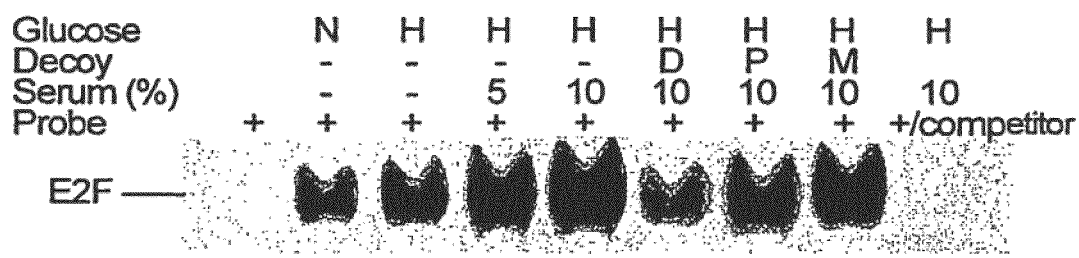
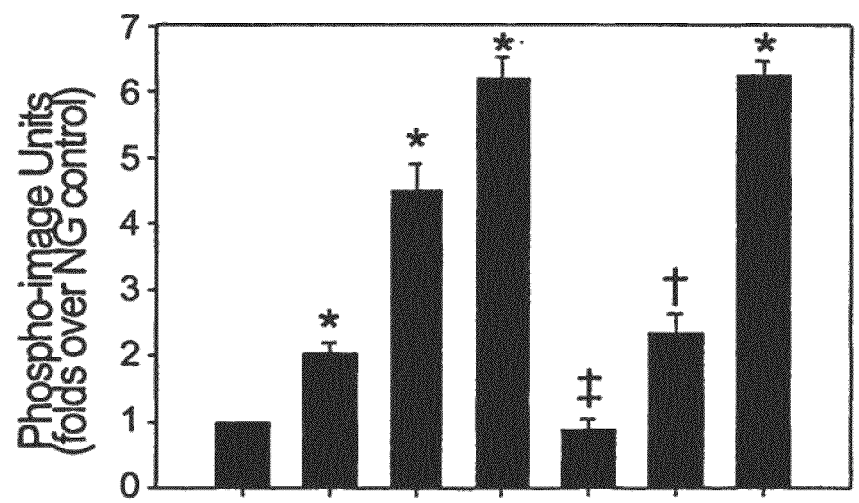

FIG. 10
A
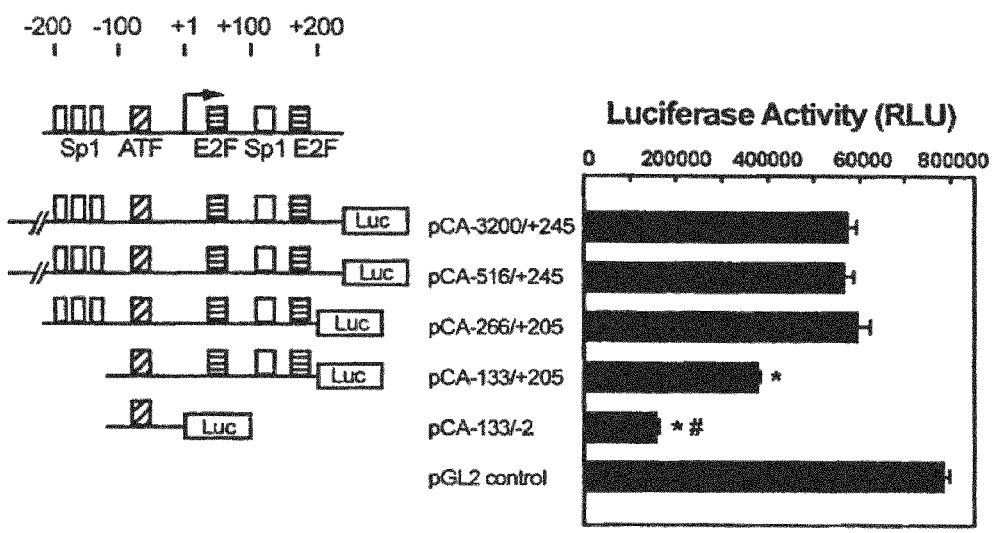
B
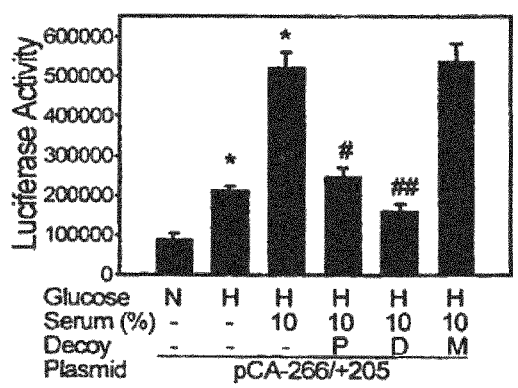
C
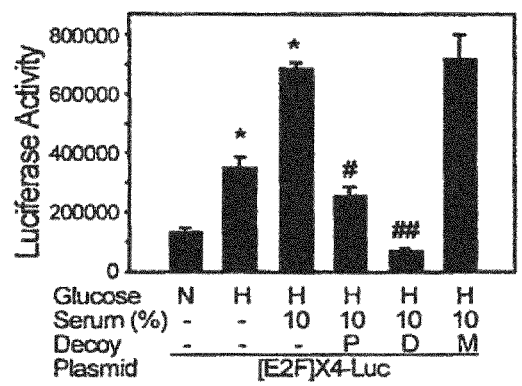

FIG. 11
A
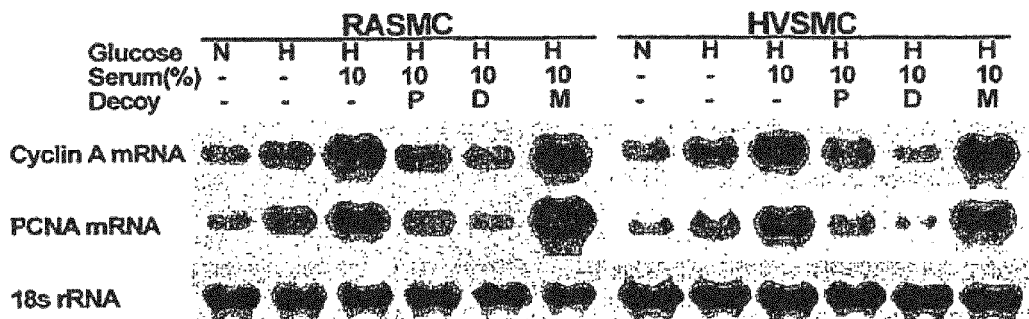
B
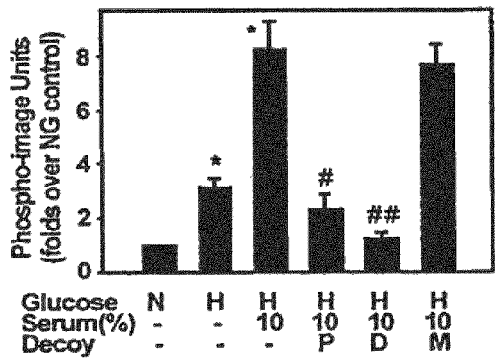
C
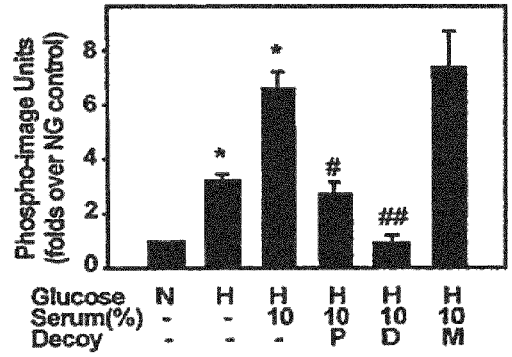
D
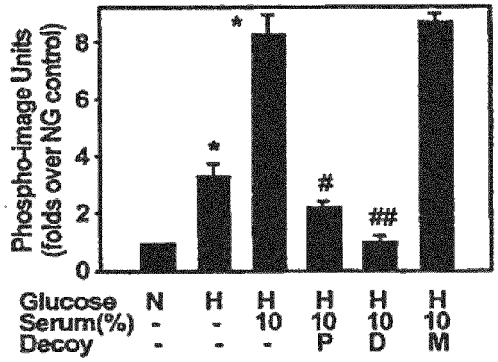
E
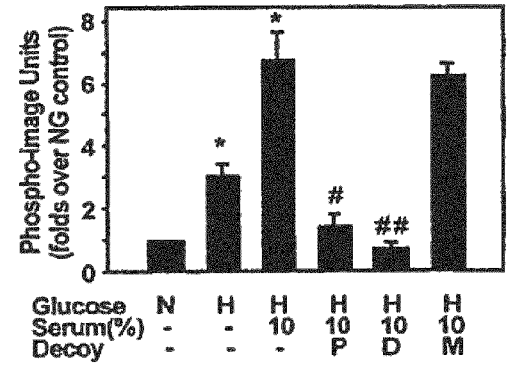

FIG. 12
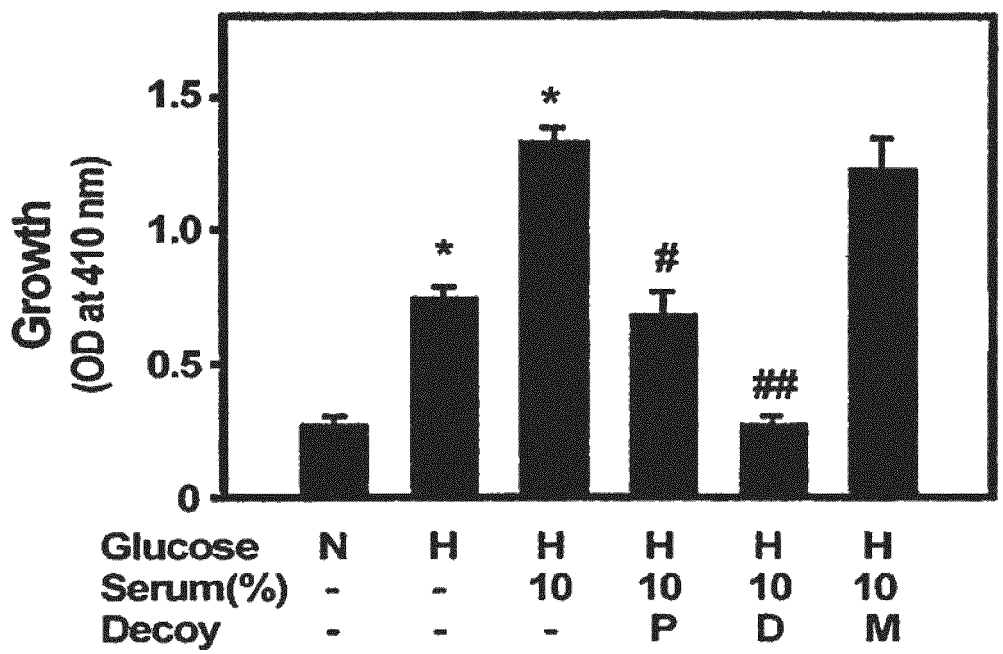
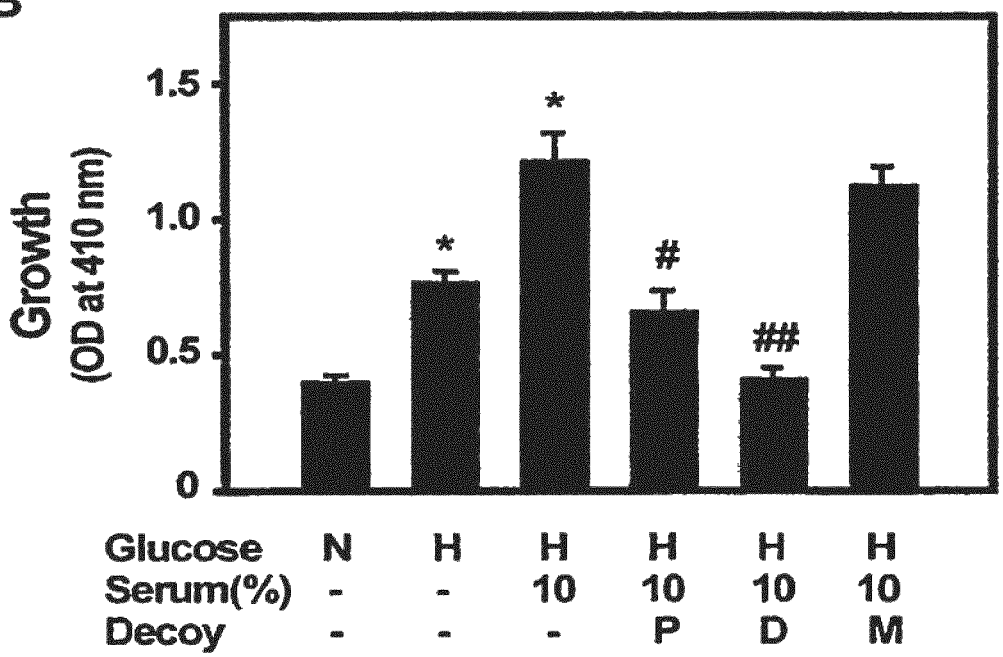

CIRCULAR DUMBBELL DECOY OLIGODEOXYNUCLEOTIDES (CDODN) CONTAINING DNA BINDINGS SITES OF TRANSCRIPTION

This application is a divisional application of U.S. patent application Ser. No. 10/512,486, filed Apr. 26, 2006 (abandoned), which is national stage application under 35 U.S.C. §371 of International Application PCT/JP02/04303, filed Apr. 26, 2002 (expired). The contents of both applications are hereby incorporated by reference in their entirety.

The instant application contains a Sequence Listing which has been submitted via EFS-Web as an ASCII text file in lieu of a paper copy and is hereby incorporated by reference in its entirety. Said ASCII text file, created on Jun. 17, 2011, is named. Sequence_Listing.txt, and is 5,685 bytes in size.

TECHNICAL FIELD

This invention is in the field of gene therapy. In particular, it is directed to novel decoy oligodeoxynucleotides and uses thereof.

BACKGROUND ART

Double stranded oligodeoxynucleotides (ODN or "decoys") for reducing trans-activity of transcription factors are an innovative and attractive strategy for gene therapy and for the functional study of gene products. Several different double-stranded DNA structures, including unmodified oligonucleotide duplexes, ab-anomeric oligonucleotides, phosphorothioate oligonucleotide duplexes, and dumbbell oligonucleotides, have been introduced as decoys for transcription factors (see Scholer H R and Gruss P., Cell 1984; 36: 403-411; Cereghini S et al. Genes Dev 1988; 2: 957-974; Berkowitz L A. et al., Mol Cell Biol 1989; 9: 4272-4281; Tanaka N as al., Nucleic Acids Res 1994; 22: 3069-3074; Bielinska A et al., Science 1990; 750:997-1000; Clusel C at al., Nucleic Acids Res 1993; 21: 3405-3411; Lim C S at al., Nucleic Acids Res 1997; 25: 575-581; Hosoya T et. al., FEBS Lett 1999; 461: 136-140; Mann M J and Dzau. V J J. Clin. Invest. 2000; 106:1071-1075).

The transfection of double-stranded cis element decoy ODNs results in the sequestration of trans-activating factors from endogenous cis-elements of the same sequence, with subsequent inhibition of gene expression (see Bielinska A, as al., 1990 supra; Morishita R, at al. 1998 supra; and Sawa Y, Morishita R, Suzuki K., Circulation 1997; 96:II-280-II-285).

Moreover, the administration of antisense or decoy oligonucleotides against NF-κB, c-myb, c-myc, cdc2, cdk2, E2F, and CRE, has been shown to decrease cachexia (Kawamura I et al, Gene Ther. 1999;6:91-97), in vitro cell proliferation and intimal thickening in experimental restenosis (see Simons M et al., Nature 1992; 359: 67-73; Morishita R at al., J Clin Invest 1994; 93:1458-1464; Morishita R et al., Proc Natl Acad Sci USA 1993; 90: 8474-8478; Morishita R et al., 1995 supra; Morishita R at al., Nat Med 1997; 3: 894-899; Kaneda Y and Morishita R, Jpn J Clin Pathol 1997;45:99-105; Tomita et al. Am. J. Physiol. 1998;275:F278-F284; Ma shima Y et al, J. Clin. Invest. 1998; 101:2589-2597; Akimoto M et al., Exp Eye Res. 1998;67:395-401; Mann M J at al., Lancet, 1999; 354:1493-1498; Mann and Dzau 2000 supra,: Kawauchi M et al, Circ. Res. 2000;87:1063-1068; Mangi A A and Dzau V J, Ann Med 2001;33:153-155; Ehsan A et al, J Thorac Cardiovasc Surg 2001;121:714-722; Kawauchi M at al. Transplant. Proc. 2001;33:451; McCarthy M, Lancet, 2001;358:1703), suppress proliferative cholangitis (Yoshida M et al, J. Surg. Res. 2002;102:95-101) and slow tumor growth and induce apoptosis in cancer models (Park Y G et al., J. Biol. Chem. 1999;274:1573-80; Cho-Chung Y S et al, Mol. Cell. Biochem. 2000;212:29-34; Alper O et al, Mol. Cell. Biochem. 2001:218:55-63), respectively.

The main limitation of unmodified oligonucleotide ODNs is that they are easily degraded by nucleases present in serum and in cells. In order to solve this problem, oligonucleotides with modified linkages such as phosphorothioate and methylphosphonate have been developed. However, these modified ODNs exhibit problems such as insensitivity to RNase H, the possibility of recycling of hydrolyzed modified nucleotides into cellular DNA, lack of sequence-specific binding effects of ODN-based gene therapy, and immune activation (see Moon I J, et al., J Biol Chem. 2000;275:4647-4653; Hosoya T, et al, FEBS Letters 1999;461:136-140; Khaled Z, et al., Nucleic Acids Res 1996; 24: 737-775; Gao W Y et al., Mol Pharmacol 1992; 41: 223-229; Brown D A et al., J Biol Chem 1994; 269: 26801-26805; and Burgess T L et al., Proc Natl Acad Sci USA 1995; 92: 4051-4055).

Recently, decoys have been proposed for treatment of diseases and disorders related to transcriptional factors including neointima formation. Neointima formation results from excessive proliferation and migration of vascular smooth muscle cells (VSMC) from media to intima, which are critical steps in the pathogenesis of atherosclerosis and restenosis which are the major problems following percutaneous transluminal coronary angioplasty (PTCA) (see Currier J W, and Faxon D P., J Am. Coll Cardiol 1995;25:516-520; Clowes A W, at al.; Lab Invest 1983;49:208-215; Liu M W, et al., Circulation 1989;79:1374-1387; Ross R., Nature. 1990;362:801-809; and Paulette P, et al., Clin. Sci. 1994;87: 467-479).

There have been a number of trials with pharmacological agents to reduce the incidence and rate of restenosis after PICA, but the results have not been satisfactory. Over the last decade, anti-gene therapy, focusing on the inhibition of VSMC proliferation, has emerged as a potentially attractive strategy for reducing restenosis after PTCA (see Simons M, et al., Nature 1992;359:67-73; Morishita R, et al., J Clin Invest 1994;93:1458-1464; Morishita R, et al., Proc Natl Acad Sci USA 1993;90:8474-8478; Morishita. R, et al, Proc Natl Acad Sci USA 1995;92:5855-5859; Morishita R, et al., Nat Med 1997;3:894-899; Morishita R et al, Pharm. Ther. 2001;91: 105-114, Motokuni A at al., Nippon Rinsho 2001;59:43-52).

Previous studies have found that extracellular signal-regulated kinase (ARK) and c-Jun $NH_2$-terminal kinase (JNK), both belonging to the mitogen-activated protein kinase (MAPK) family, are rapidly and transiently activated after balloon-injury (see Ohashi N, et al., Arterioscler Thromb Vase Biol. 2000;20:2521-252:6; Koyama H, et al., Circ Res. 1998;82:713-721; Hu Y, et al., Arterioscler Thromb Vase Biol. 1997;17:2808-2816; and Pyles J M, et al., Circ Res. 1997;81:904-910).

ERK2 and JNK1 activities in the injured vessel wall rapidly increase after balloon injury and reach a high level at 5 minutes after injury. A sustained increase in ERK2 kinase activity was observed over the next 7 days in the arterial wall and 14 days in neointima after injury (Hu Y, et al, 1997 supra; and Izumi Y, et al., Circ Res. 2001:88:1120-1126).

JNK and ERK are known to be translocated into the nucleus, and activate c-Jun and c-Fos, which dimerize to form the transcription factor complex AP-1. AP-1 binds to specific DNA sequences present in a large number of genes associated with a diverse range of cell proliferative responses such as extracellular matrix production (see Karin M., J Biol Chem. 1995;270:16483-16486; and Whitmarch J. and Davis R J., J Mol Med. 1996;74:589-607), apoptosis (Le-Niculescu H et al., Mol. Cell. Biol. 1999;19:751-763; Taimor G. et al., FASEB J. 2001;15:2518-2520), vascular remodeling (Morishita R, et al., Biochem Biophys Res Common 1998;243: 361-367; Lauth M. et al., J Mol Med 2000;78:441-450; Wagner A H et al., Mol. Pharm. 2000;58:1333-1340; Cattaruzza M. et al., J. Biol. Chem. 2001;276:36999-37003), COX-2 mediated inflammation (Adderley, S R and Fitzgerald D J, J. Biol. Chem 1999;274:5038-5046; von Knethen A et al., Mol. Biol. Cell 1999;10:361-372; von Knethen A et al., J. Immunology 1999;163:2858-2866; Subbaramaiah K et al., J. Biol. Chem. 2001;276:12449-12448) and production of type 1 plasminogen activator inhibitor (PAI-1) (Ann J D., et al., Diabetologia 2001;44:713-720) TGF-0 (Sin G and Howe P H, J. Biol. Chem. 1997;272:26620-26626) and IL-6 (Viedt C et al., FASEB J 2000;14:2370-2372).

These results suggest that AP-1 binding may be involved in vascular smooth muscle cell proliferation in response to vascular injury. However, it is not known whether inhibition of AP-1 binding would prevent neointima formation.

Recent reports have also shown that the transcription factor E2F, which forms a complex with cyclin A, cdk2, and pRB, and activates and phosphorylates these cell cycle regulatory genes, is critical to the process of cell growth and proliferation (see Pagano N at al. EMBO J 1992; 11: 961-971; Pardee A B. Proc Natl Acad. Sci USA 1974; 71: 1286-1290; Weintraub S J, et al. Nature 1992; 358: 259-261; Pagano M G, at al. Science 1992; 255: 1144-1147; and Rosenblatt J, at al. Proc Natl Acad Sci USA 1992; 89: 2824-2828).

The transcriptional factor nuclear factor-κB (NFκB) plays a pivotal role in the coordinated transactivation of cytokine and adhesion molecule genes that might be involved in myocardial damage after ischemia and reperfusion. Decoys specific for NFkB has been used in vivo to bind the transcriptional factor and to block the activation of genes mediating myocardial infarction, thus providing effective therapy for myocardial infarction (Morishita R. et al., Nat Med 1997 August; 3(8):894-9).

Although there have been successful application of decoys to some diseases and disorders related to transcriptional factors, the above-mentioned main limitation of unmodified oligonucleotide ODNs where they are easily degraded by nucleases present in serum and in cells, significantly reduces the efficacy of decoys in treatment and prevention of such diseases and disorders.

In in vitro studies, covalently closed ODNs have been developed to avoid exonuclease activities by enzymatically ligating two identical molecules, in order to overcome these limitations. Circular dumbbell oligonucleotides, which are made by the circularization of the oligonucleotides by joining the 3' and the 5' ends with enzymatic ligations, and have a non-toxic unmodified backbone which resembles natural DNA, have increased stability to exonucleases, had have increased uptake into cells as compared with the chemically modified linear oligonucleotides (See Chu B C F and Orgal L., Nucleic. Acids Res. 1992; 20:5857-5858; and Abe T, et al., FEBS Lett. 1998; 425:91-96).

However, there have been no reports showing that such covalently closed ODNs or circular dumbbell oligonucleotides are effective in treating or preventing diseases or disorders.

Problem to be Solved by the Invention

Therefore, an object of the invention is to provide more efficient and effective means for treating and preventing diseases and disorders related to a transcriptional factor.

Further, an object of the invention is to provide means such as a decoy ODN containing a transcriptional factor such as AP-1 binding site for transfection of VSMC, which would cause the decoy to effectively bind AP-1, prevent the transactivation of essential genes associated with cell proliferative response and thereby inhibit neointima formation.

Another object of the present invention is thus to provide novel AP-1 decoy ODNs with circular dumbbell-structure (CDODN), to clarify the role of AP-1 activation in balloon injury. The AP-1 decoy ODN with circular dumbbell-structure (CDODN) can be transfected using hemagglutinating virus of Japan (HVJ)-liposomes. In this invention, we evaluated the stability and effectiveness of CDODN in vitro as well as in vivo. Here, we demonstrate that AP-1 activation plays a critical role in the VSMC proliferation in response to injury and that the transfection of rat arteries with the novel CDODN, before a balloon injury procedure, almost completely prevents neointima formation in balloon-injured rat arteries.

A further object of the present invention to develop a novel therapeutic strategy for restenosis following angioplasty comprising administering to a patient prior to, during or following angioplasty, an effective amount of a CDODN AP-1 decoy or other AP-1 inhibitory compound.

A still further object of the present invention is to provide a novel E2F decoy, which was made by covalent closure of the two identical oligo molecules to avoid exonuclease digestion. We investigated the stability and the sequence specific inhibition effect of this circular dumbbell E2F decoy (CD-E2F) on the transactivation of essential cell cycle-regulatory genes and on the inhibition of VSMC proliferation and neointima formation.

A yet further object of the present invention is to develop a novel therapeutic strategy for restenosis following angioplasty comprising administering to a patient prior to, during or following angioplasty, an effective amount of a CD-E2F decoy.

DISCLOSURE OF THE INVENTION

Summary of the Invention

The present invention provides a circular dumbbell oligodeoxynucleotide (CDODN) comprising two loop structures and a stem structure, wherein the stem structure comprises a nucleotide sequence capable of binding the DNA-binding domain of a transcriptional factor. The present invention further provides a pharmaceutical composition comprising said CDODN. The pharmaceutical composition can be used for treating and/or preventing a disease or disorder related to such a transcriptional factor. The present invention also provides a method for treating and/or preventing a disease or disorder related to such a transcriptional factor, comprising administering to the subject a therapeutically effective amount of a CDODN comprising two loop structures and a stem structure, wherein the stem structure comprises a nucleotide sequence capable of binding the DNA-binding domain of the transcriptional factor.

Preferably, the transcriptional factor may be selected from the group consisting of NFκB, STAT-1, GATA-3, STAT-6, AP-1, E2F, E2F and CRE. Preferably, a NF-κB decoy may comprise the sequence 5'-CCTTGAAGGGATTTCCCTCC-3' (Seq ID No. 9) (NF-κB decoy); a STAT-1 decoy may comprise the sequence 5'-GATCTAGGGATTTCCGG-GAAATGAAGCT-3' (Seq. ID No. 10) (STAT-1 decoy); a GATA-3 decoy may comprise the sequence 5'-AGCT-TGAGATAGAGCT-3' (Seq. ID No.11) (GATA-3 decoy); a STAT-5 decoy may comprise the sequence 5'-GATCAA-GACCTTTTCCCAAGAAATCTAT-3' (Seq. ID No. 12) (STAT-6 decoy); an AP-1 decoy may comprise the sequence 5'-AGCTTGTGAGTCAGAAGCT-3' (Seq. ID No. 13) or 5'-TGACTCA-3' (AP-1 decoy); an ets decoy may comprise the sequence 5'-AATTCACCGGAAGTATTCGA-3' (Seq. ID No. 14) (Ets decoy); a CRE decoy may comprise the sequence 5'-TGACGTCA-3' (CRE decoy); and an E2F decoy may comprise the sequence 5'-TTTCGCGC-3' (E2F decoy.

Excessive proliferation of vascular smooth muscle cells and neointima formation are critical steps in the pathogenesis of atherosclerosis and restenosis following percutaneous transluminal angioplasty. In order to show the efficacy of CDODN for AP-1 in the treatment or prevention of such a disease or disorder, the following study was undertaken to test our hypothesis that the transcription factor AP-1 plays an important role in these processes and to develop a novel therapeutic strategy for restenosis following angioplasty. Overall, our results showed that AP-1 activation is crucial in mediating smooth muscle cell proliferation in response to vascular injury. Therefore the present invention provides a novel strategy for preventing smooth muscle cell proliferation leading to restenosis.

We developed a novel AP-1 decoy ODN with a circular dumbbell structure (CDODN) to avoid destruction by exonucleases. This new form of AP-1 decoy ODN was more stable, largely preserving its structural integrity after incubation in the presence of either exonuclease III or serum, than phosphorothioate linear decoy ODN (PSODN). Transfection of AP-1 decoy ODN strongly inhibited both proliferation and migration of vascular smooth muscle cells. AP-1 decoy ODN also inhibited high glucose- and serum-induced transcriptional expression of PCNA and cyclin A genes. Consistent with in vitro data, administration of AP-1 decoy ODN in vivo using the Hemagglutinating virus of Japan (HVJ)-liposome method almost completely inhibited neointima formation after balloon injury of rat carotid artery. As compared to conventional PSODN, CDODN was more effective in the inhibition of proliferation of smooth muscle cells in vitro and neointima formation in vivo. Approximately half the dose of CDODN, as compared to PSODN, was enough to obtain similar effects on growth inhibition of vascular smooth muscle cells in vitro as well as in vivo. Moreover, the sequence specificity of the CDODN of AP-1 binding was unexpectedly more 10 times greater than conventional PSODN.

This invention thus shows that employment of a more stable CDODN against AP-1 with the highly effective HVJ-liposome delivery method provides a new therapeutic strategy for the prevention of restenosis after angioplasty in humans.

Further, the present invention is concerned with the transcription factor E2F which plays a critical role in the transactivation of several genes involved in cell-cycle regulation. Previous studies have shown that the transfection of cis element double stranded oligodeoxynucleotides (decoys), corresponding to E2F binding domains, could inhibit vascular smooth muscle cell (VSMC) proliferation and an ointimal hyperplasia in injured vessels. In the present study, we developed a novel E2F decoy with a circular dumbbell structure (CD-E2F) and compared the effect of this CD-E2F with conventional phosphorothioated E2F decoy (PS-E2F). We found that the CD-E2F was more stable, largely preserving its structural integrity after incubation in the presence of either nucleases or serum, than PS-E2F. The CD-E2F more strongly inhibited high glucose- and serum-induced transcriptional expression of cell-cycle regulatory genes as compared with the PS-E2F. Transfection of CD-E2F was more effective in the inhibition of VSMC proliferation as well as neointima formation in vivo, as compared with PS-E2F. CD-E2F in a 40-50% reduced dose compared. with PS-E2F was enough to obtain a similar effect on VSMC growth inhibition in vitro as well as neointima formation in vivo. Moreover, CD-E2F unexpectedly showed a 10 times greater sequence specificity against E2F than PS-E2F.

In conclusion, our results show that CD-E2F is a more valuable agent for gene therapy to inhibit VSMC proliferation, for example in the treatment of restenosis following angioplasty, and for the study of transcriptional regulation, than conventional E2F decoys.

Means for Solving the Problem

The present invention provides the following:
1. A circular dumbbell oligodeoxynucleotide (CDODN) comprising two loop structures and a stem structure, wherein the stem structure comprises a nucleotide sequence capable of binding the DNA-binding domain of a transcriptional factor.
2. The CDODN according to item 1, wherein said transcriptional factor is selected from the group consisting of NFκB, STAT-1. GATA-3, STAT-6, AP-1, E2F, Ets and CRE.
3. The CDODN of item 1, which comprises two identical stem loop structures covalently linked by enzymatic ligation.
4. The CDODN of item 1, which does not contain any chemically modified nucleotides.
5. The CDODN of item 1, which stem structure additionally comprises nucleotide sequences capable of binding the DNA-binding domain of two or more transcription factors.
6. The CDODN according to item 1, said transcriptional factor is AP-1.
7. The CDODN of item 6, wherein the nucleotide sequence capable of binding the DNA-binding domain of AP-1 is 5'-TGACTCA-3'.
8. The CDODN of item 6, wherein each of the identical stem loop structures has the sequence of SEQ ID. NO. 3.
9. The CDODN of item 6, which stem structure additionally comprises a nucleotide sequence capable of binding the DNA-binding domain of another transcription factor.
10. The CDODN of item 6, which has an AP-1 sequence specificity of greater than about 5 times that of a phosphorothiolated oligonucleotide with the sequence of SEQ ID. NO. 4, as assessed by in vitro competitive binding assay.
11. The CDODN of item 1, wherein said transcriptional factor is E2F.
12. The CDODN of item 11, wherein the nucleotide sequence capable of binding the DNA-binding domain of E2F is 5'-TTTCGCGC-3'.
13. The CDODN of item 11, wherein each of the identical stem loop structures has the sequence of SEQ ID. NO. 6.
14. The CDODN of item 11, which has an E2F sequence specificity of greater than about 5 times that of a phosphorothiolated oligonucleotide with the sequence of SEQ ID. NO. 7, as assessed by in vitro competitive binding assay.
15. The CDODN of item 1, wherein said transcriptional factor is NFκB.
16. A method for treating or preventing a disease or disorder related to a transcriptional factor in a subject, comprising administering to the subject a therapeutically effective amount of a CDODN comprising two loop structures and a stem structure, wherein the stem structure comprises a nucleotide sequence capable of binding the DNA-binding domain of the transcriptional factor.

17. The method according to item 16, wherein said transcriptional factor is selected from the group consisting of NFκB, STAT-1, GATA-3, STAT-6, AP-1, E2F, Ets and CRE.
18. The method of item 16, where the pharmaceutically acceptable carrier is a HVJ-liposome composition.
19. The method according to item 16, wherein said transcriptional factor is AP-1.
20. The method according to item 18, wherein the disease or disorder related to a transcriptional factor comprises vascular smooth muscle cell proliferation or neointimal hyperplasia in the subject following vessel injury.
21. The method of item 19, where the amount of the CDODN is sufficient to prevent restenosis in the subject.
22. The method of item 20, where the compound is administered prior to the vessel injury.
23. The method of item 16, wherein said transcriptional factor is E2F.
24. The method of item 23, wherein said disease or disorder comprises vascular smooth muscle cell proliferation or neointimal hyperplasia in the subject following vessel injury.
25. The method of item 23, wherein the therapeutically effective amount of the CDODN is effective to prevent restenosis in the subject.
26. The method of item 24, wherein the CDODN is administered after the vessel injury.
27. The method of item 16, wherein said transcriptional factor is NFκB.
28. The method of item 16, wherein said disease or disorder comprises inflammatory bowel disease.
29. A pharmaceutical composition for treating or preventing a disease or disorder related to a transcriptional factor in a subject, comprising a therapeutically effective amount of a CDODN comprising two loop structures and a stem structure, wherein the stem structure comprises a nucleotide sequence capable of binding the DNA-binding domain of the transcriptional factor, and a pharmaceutically acceptable carrier.
30. The pharmaceutical composition according to item 29, wherein said transcriptional factor is selected from the group consisting of NFκB, STAT-1, GATA-3, STAT-6, AP-1, E2F, Ets and CRE.
31. The pharmaceutical composition of item 29, where the pharmaceutically acceptable carrier is a HVJ-liposome composition.
32. The pharmaceutical composition according to item 29, wherein said transcriptional factor is AP-1.
33. The pharmaceutical composition according to item 29, wherein said disease or disorder is vascular smooth muscle cell proliferation or neointimal hyperplasia in the subject following vessel injury.
34. The pharmaceutical composition of item 29, where the amount of the CDODN is sufficient to prevent restenosis in the subject.
35. The pharmaceutical composition according to item 29, wherein said transcriptional factor is E2F.
36. The pharmaceutical composition according to item 35, wherein said disease or disorder is vascular smooth muscle cell proliferation or neointimal hyperplasia in the subject following vessel injury.
37. The pharmaceutical composition of item 36, wherein the therapeutically effective amount of the CDODN is effective to prevent restenosis in the subject.
38. The pharmaceutical composition of item 29, wherein said transcriptional factor is NFκB.
39. The pharmaceutical composition item 29, wherein said disease or disorder comprises inflammatory bowel disease.
40. Use, in the manufacture of a medicament for treating or preventing a disease or disorder related to transcriptional factor in a subject, of a therapeutically effective amount of a CDODN comprising two loop structures and a stem structure, wherein the stem structure comprises a nucleotide sequence capable of binding the DNA-binding domain of the transcriptional factor.
41. The use according to item 40, wherein said transcriptional factor is selected from the group consisting of NFκP, STAT-1, GATA-3, STAT-6, AP-1, E2F, Ets and CRE.
42. The use according to item 40, wherein said medicament is in the form of a HVJ-liposome composition.
43. The use according to item 40, wherein said transcriptional factor is AP-1.
44. The use according to item 43, wherein said disease or disorder is vascular smooth muscle cell proliferation or neointimal hyperplasia in the subject following vessel injury.
45. The use according to item 43, wherein the amount of the CDODN is sufficient to prevent restenosis in the subject.
46. The use according to item 40, wherein said transcriptional factor is E2F.
47. The use according to item 46, wherein said disease or disorder is vascular smooth muscle cell proliferation or neointimal hyperplasia in the subject following vessel injury.
48. The use of item 40, wherein the therapeutically effective amount of the CDODN is effective to prevent restenosis in the subject.
49. The use of item 40, wherein said transcriptional factor is NFκB.
50. The use item 46, wherein said disease or disorder comprises inflammatory bowel disease.

In another aspect of the invention, the present invention further provides a method for treating a disease or disorder related to AP-1, comprising administering to the subject a therapeutically effective amount of a compound able to inhibit trans-activation of genes for mitogen-activated protein kinases by AP-1, and a pharmaceutically acceptable carrier.

Further, the present invention provides a method of preventing vascular smooth muscle cell proliferation or neointimal hyperplasia in a subject following vessel injury, comprising administering to the subject a therapeutically effective amount of a compound able to inhibit trans-activation of genes for mitogen-activated protein kinases by AP-1, and a pharmaceutically acceptable carrier.

In one embodiment of the invention, the compound may inhibit the ability of said AP-1 to bind the promoters of said genes.

In one embodiment of the invention, the compound may be an antibody, or a nucleic acid or a nucleic acid analog.

In one embodiment of the invention, the compound may competitively inhibit binding of the AP-1 to the promoters.

In a preferable embodiment of the invention, the compound is a circular dumbbell oligodeoxynucleotide (CDODN) comprising two loop structures and a stem structure, wherein the stem structure comprises a nucleotide sequence capable of binding the DNA-binding domain of AP-1.

In one embodiment of the Invention, the amount of the CDODN may be sufficient to prevent restenosis in the subject.

In one embodiment of the invention, the pharmaceutically acceptable carrier may be a HVJ-liposome composition.

In another aspect of the invention, the present invention provides a pharmaceutical composition for preventing vascular smooth muscle cell proliferation or neointimal hyperplasia in a subject following vessel injury, comprising a therapeutically effective amount of a compound able to inhibit trans-activation of genes for mitogen-activated protein kinases by AP-1, and a pharmaceutically acceptable carrier.

In one embodiment of the invention, the compound may inhibit the ability of said AP-1 to bind the promoters of said genes.

In one embodiment of the invention, the compound may be an antibody, or a nucleic acid or a nucleic acid analog.

In one embodiment of the invention, the compound may competitively inhibit binding of said AP-1 to said promoters.

In a preferable embodiment of the invention, the compound may be a circular dumbbell oligodeoxynucleotide (CDODN) comprising two loop structures and a stem structure, wherein the stem structure comprises a nucleotide sequence capable of binding the DNA-binding domain of AP-1.

In one embodiment of the invention, the amount of the CDODN may be sufficient to prevent restenosis in the subject.

In one embodiment of the invention, the pharmaceutically acceptable carrier may be a HVJ-liposome composition.

In another aspect of the invention, the present invention provides use, in the manufacture of a medicament for preventing vascular smooth muscle cell proliferation or neointimal hyperplasia in a subject following vessel injury, of a therapeutically effective amount of a compound able to inhibit trans-activation of genes for mitogen-activated protein kinases by AP-1.

In one embodiment of the invention, the compound inhibits the ability of said AP-1 to bind the promoters of said genes.

In one embodiment of the invention, the compound is an antibody, or a nucleic acid or a nucleic acid analog.

In one embodiment of the invention, the compound competitively inhibits binding of said AP-1 to said promoters.

BRIEF DESCRIPTION OF THE DRAWINGS

FIG. 3 shows effects of CDODN on gene expression in smooth muscle cells. [A] Cells were cotransfected with the decoy ODNs and serial deletion or mutation constructs of cyclin A promoter under high glucose condition in smooth muscle cells. $*p<0.001$ compared to pCA-266/+205, $\dagger p<0.001$ compared to pCA-133/+205. [B] and [C] Cells were cotransfected with the decoy ODNs and plasmid AP1 (PMA)-TA-Luc (B), or pCA-266/+205 (C). The activity of the decoy ODNs is reflected in their ability to down-regulate luciferase activity. Values are mean±SEM of six independent experiments after normalization of β-galactosidase activity. $*p<0.01$ compared to NG, $\dagger p<0.01$ compared to HG+10% serum, $\ddagger p<0.001$ compared to HG+10% serum. D, Representative Northern blot analysis. Gene expression of cyclin A (upper panels) and PCNA (lower panels) was measured by northern blotting in RASMC (left panels) or HVSMC (right panels).

N; VSMC cultured with normal glucose (5.5 mmol/l D-glucose), H; VSMC cultured with high glucose (25 mmol/l D-glucose), Decoy ODN; VSMC transfected with 100 nmol/l AP-1 decoy ODNs, P; PSODN, D; CDODN, M; mismatch AP-1 decoy ODN.

FIG. 4 shows the effect of CDODN on inhibition of cell proliferation in HVSMC (A) and RASMC (B). Proliferation activities are means±SEM of 6 measurements. Effect of CDODN on cell migration in HVSMC (C) and RASMC (D). Average number of cells from 4 randomly chosen high-power (×400) fields on the lower surface of the filter was counted. Each experiment was performed in triplicate, and 4 independent experiments were performed. Migration activities are means±SEM.

N; VSMC cultured with normal glucose (5.5 mmol/l D-glucose), H; VSMC cultured with high glucose (25 mmol/l D-glucose), Decoy ODN; VSMC transfected with 100 nmol/l AP-1 decoy ODNs, P; PSODN, D; CDODN, M; mismatch AP-1 decoy ODN. $*p<0.01$ compared to NG, $\dagger p<0.05$ compared to HG+10% serum, $*p<0.01$ compared to HG+10% serum.

Figure 5:
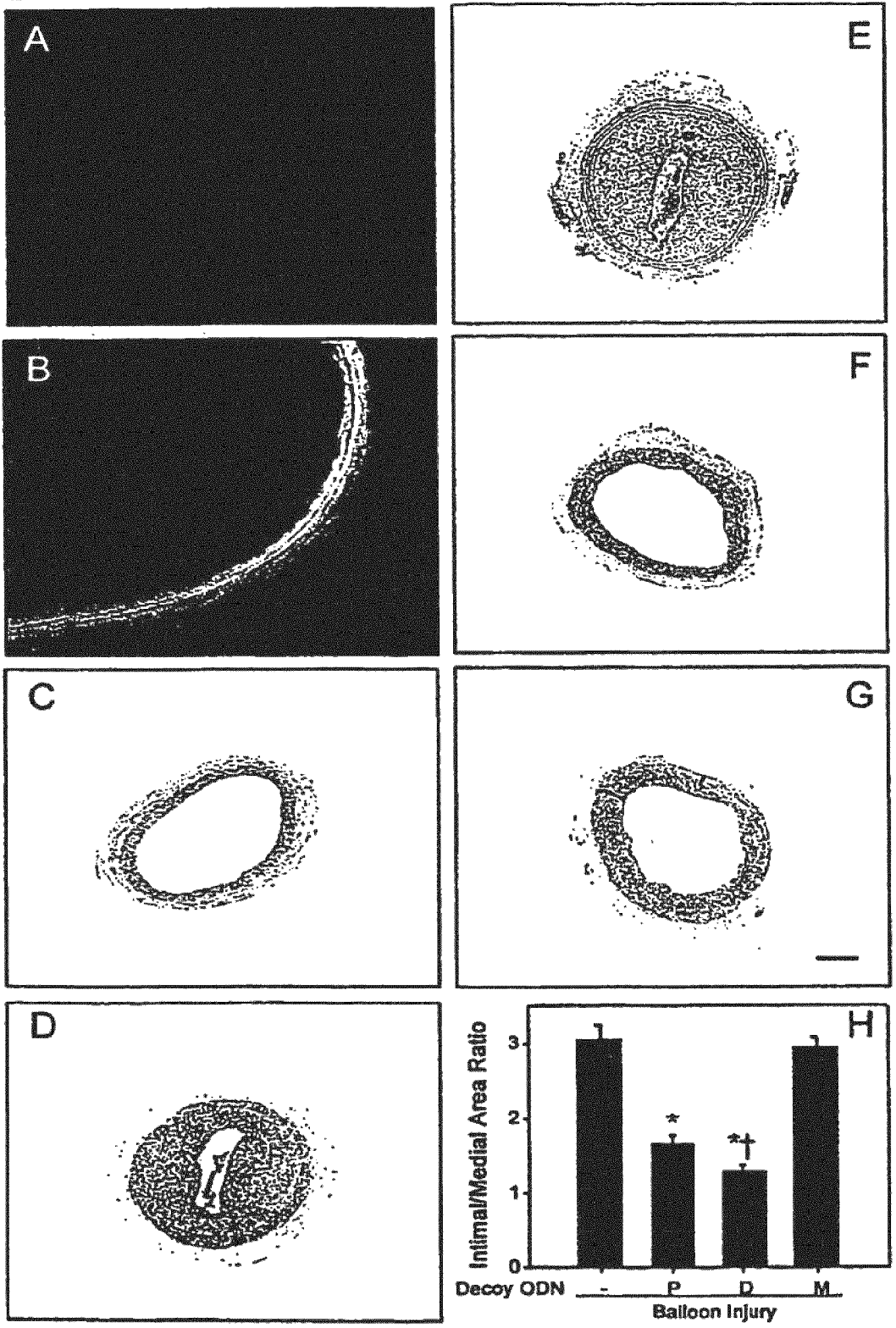

FIG. 5 shows the effect of AP-1 decoy ODNs on neointima formation after balloon injury in rat carotid arteries. (A)+(B) Fluorescence microscopy of the left common carotid artery: treated with FITC-labeled ODN only (A), or treated with FITC-labeled ODN with HVJ-AVE liposomes (B); (C)-(G) cross-sections of the left common carotid artery of: control rat (C), 14 days after balloon injury (D), (E)-(G)—14 days after balloon injury treated with: MODN using HVJ-AVE liposome method (E)» with PSODN (F), and with CDODN (G). (H) Average ratio of intimal/medial area of the left carotid artery in groups transfected with HVJ-liposomes containing AP-1 decoy ODNs. Bars represent neointima/media ratio of common carotid arteries after balloon injury from each group of animals studied (n=10). Values are means±SEM. $*p<0.01$ compared to balloon injured arteries, $\dagger p<0.05$ compared to PSODN treated arteries.

Figure 6:
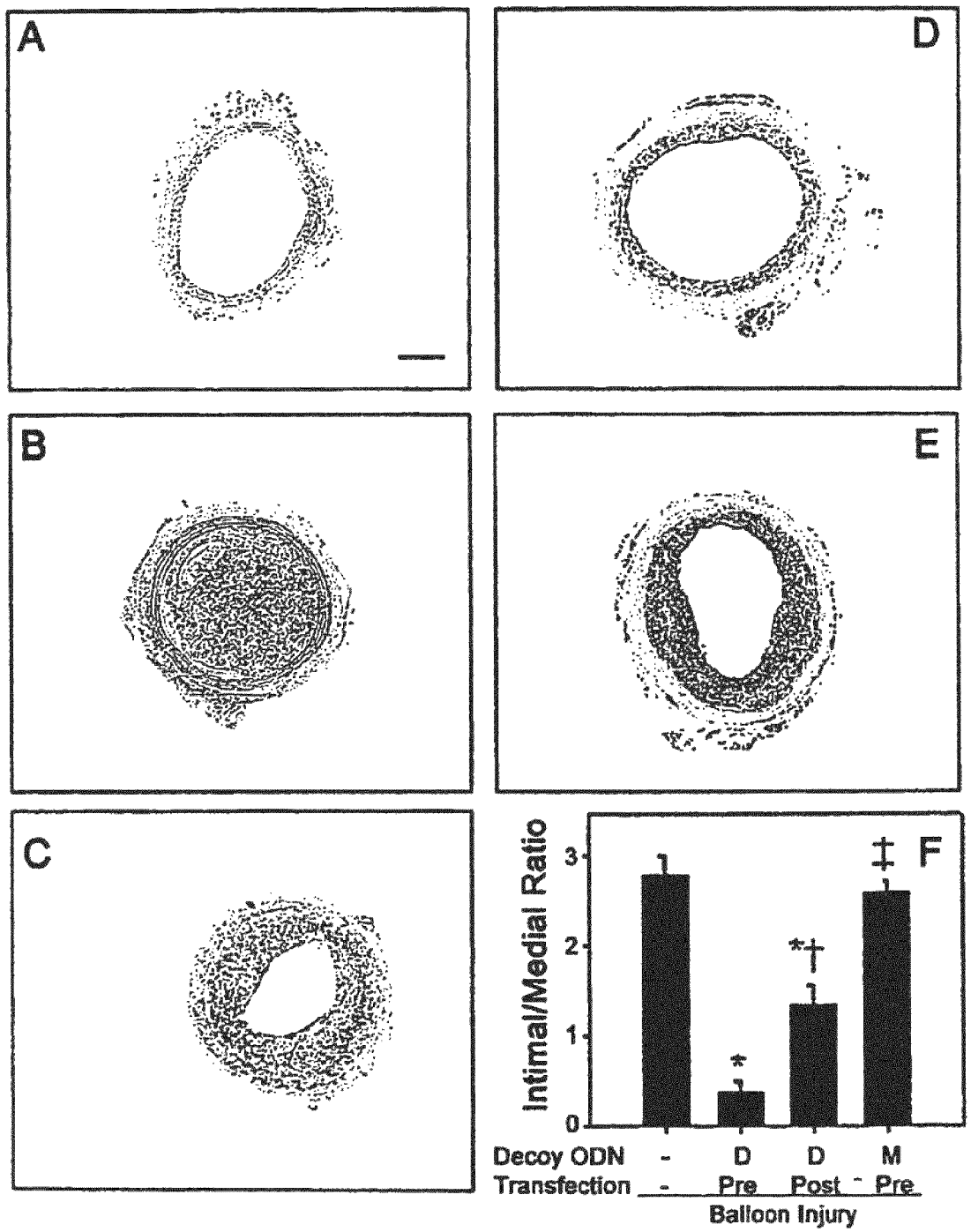

FIG. 6 shows the effect of CDODN treatment time point on inhibition of neointima formation in injured carotid arteries. (A)-(E) Cross section of the left common carotid artery of: control rat (A), 14 days after balloon injury (B), pre-treatment of MODN using HVJ-AVE liposome method (C), pre-treatment of CDODN (D), and post-treatment of CDODN (E). (F) Average ratio of intimal/medial area of the left carotid artery in groups transfected with HVJ-liposomes containing AP-1 decoy ODNs. Bars represent neointima/media ratio of common carotid arteries after balloon injury from each group of animals studied (n=10). Values are means±SEM. *p<0.005 compared to balloon injured arteries, †p<0.01 compared to arteries pre-treated with CDODN, †p<0.01 compared to arteries post-treated with CDODN.

Figure 7:
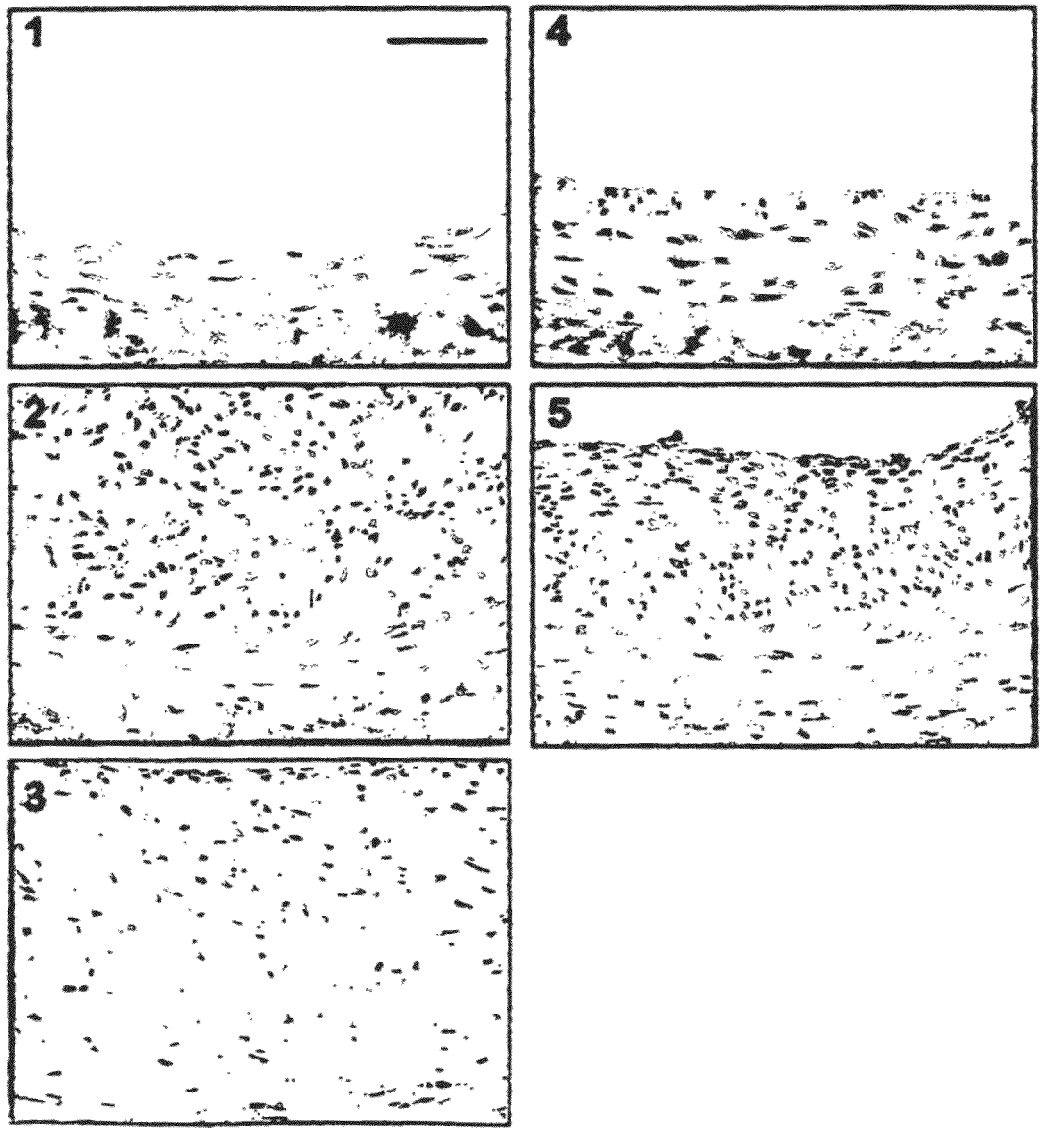

FIG. 7A shows the analysis of AP-1 binding activity in arterial extracts. Gel mobility shift assays were performed using nuclear extracts of cells from carotid arteries at the indicated time points following injury (n=10). Before (Pre-treated CDODN) or after (Post-treated CDODN) balloon injury, 20 μl of HVJ-liposomes complex containing CDODN was incubated within the lumen for 10 min at room temperature. FIG. 7B shows the PCNA expression in rat carotid artery after balloon injury. PCNA staining of control vessel (1), balloon injured vessel (2), pre-treated arteries with MODN (3), pre-treated arteries with CDODN (4), and post-treated arteries with CDODN (5). PCNA positive cells positive appear as brownish-black. All figures at 400× magnification.

FIG. 8 shows the structure and molecular stability of E2F decoys: PSODN (SEQ ID NO: 7 and SEQ ID NO: 24), Annealed form (SEQ ID NO: 26), CDODN (SEQ ID NO: 6), and MODN (SEQ ID NO: 8). [A] Structure of E2F decoy consisting of two identical stem loops covalently ligated to form the CD-E2F molecule. CD-E2F consists of two binding sites for E2F on its stem region. [B] Stability of decoys in the presence of exonuclease III (left panel), SI nuclease (left panel), or serum (right panel). Abbreviations: Exo III; decoy treated with exonuclease III, S1; decoy treated with S1 nuclease, CS; calf serum, D; CD-E2F, P; PS-E2F, and L; the annealed form of CD-E2F prior to ligation.

FIG. 9 Effects of CD-E2F on the DNA binding activity of E2F. [A] Amounts of E2F complexes formed between labeled probe and the E2F protein in the presence of various concentrations of unlabeled ODN. [B] A typical example of a gel shift assay is shown for VSMCs transfected with E2F decoy. The experiment was repeated six times. Abbreviations: NG; normal glucose (5.5 mmol/l D-glucose), HG; high glucose (25 mmol/l D-glucose). Decoy ODN; VSMCs transfected with 100 nmol/l E2F decoy, P; PS-E2F, D; CD-E2F, and M; M-E2F. EMSA results are expressed as the mean± SEM of five independent experiments. Statistical significance was determined as *p<0.001 compared to NG, †p<0.01 compared to HG+10% serum, ‡p<0.05 compared to PS-E2F.

FIG. 10 shows the effects of CD-E2F on promoter activity of cell-cycle-related genes in smooth muscle cells. (A) VSMCs were cotransfected with decoy and serial deletion or mutation constructs of cyclin A promoter under high glucose conditions. Statistical significance was determined as *p<0.01 compared to pCA-266/+205, †p<0.01 compared to pCA-133/+205. VSMCs were cotransfected with decoy and plasmid pCA-266/+205 (B) or [E2F]×4-ILuc (C). The activity of decoy is reflected in their ability to down-regulate luciferase activity. Values represent the means±SEM of five independent experiments after normalization of β-galactosidase activity. Statistical significance was determined as *p<0.01 compared to NG, #p<0.01 compared to HG+10% serum, ##p<0.05 compared to PS-E2F.

Abbreviations: N; VSMC cultured with normal glucose (5.5 mmol/l D-glucose), H; VSMC cultured with high glucose (25 mmol/l D-glucose), Decoy ODN; VSMC transfected with 100 nmol/l E2F decoy, P; PS-E2F. D; CD-E2F, M; M-E2F.

FIG. 11 shows the effects of CD-E2F on gene expression in VSMCs. (A) Representative Northern blot analysis. Gene expression of cyclin A (B and C) and PCNA (D and E) in RASMC (B and D) or HVSMC (C and E) was quantified using densitometric analysis.

Abbreviations: N; VSMC cultured with normal glucose (5.5 mmol/l D-glucose), H; VSMC cultured with high glucose (25 mmol/l D-glucose), Decoy ODN; VSMC transfected with 100 nmol/l E2F decoy, P; PS-E2F, D; CD-E2F, M; M-E2F. Values represent the means±SEM of five independent experiments. Statistical significance was determined as *p<0.01 compared to NG, #p<0.001 compared to HG+10% serum, ##p<0.05 compared to PS-E2F.

FIG. 12 shows the effects of CD-E2F on inhibition of cell proliferation in HVSMC (A) and RASMC (B). Proliferation activities are means±SEM of 6 measurements. Decoys were transfected into smooth muscle cells. 2-3 days after transfection, an index of cell proliferation was determined with the use of a WST cell counting kit. Statistical significance was determined as *p<0.01 compared to NG, #p<0.01 compared to HG+10% serum, and ##p<0.05 compared to PS-E2F.

Abbreviations: N; VSMC cultured with normal glucose (5.5 mmol/l D-glucose), H; VSMC cultured with high glucose (25 mmol/l D-glucose), Decoy ODN; VSMC transfected with 100 nmol/l E2F decoy, P; PS-E2F, D; CD-E2F, M; M-E2F.

Figure 13:
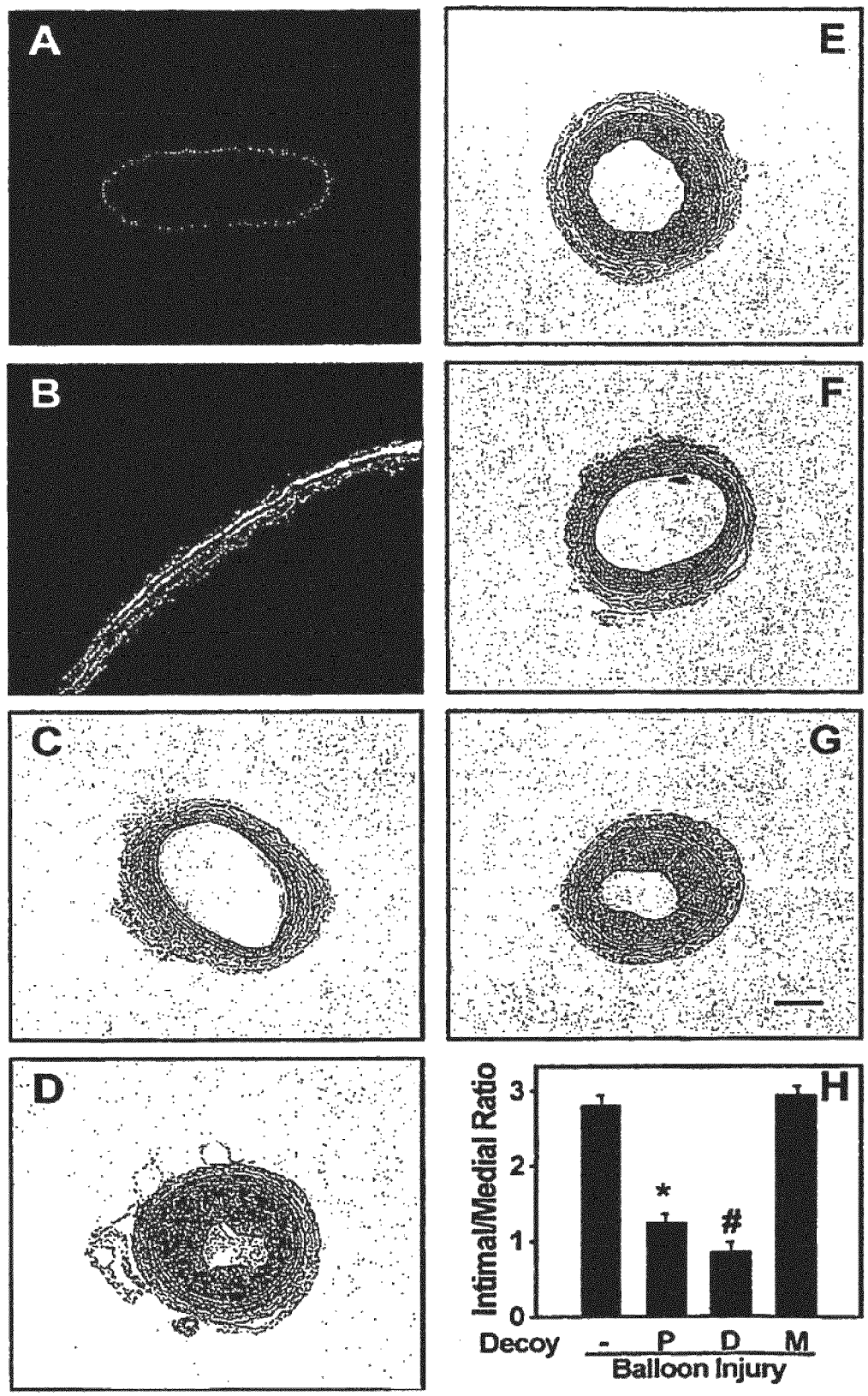

FIG. 13 Effects of E2F decoy on neointima formation occurring after balloon injury in rat carotid artery. The illustration depicts fluorescence microscopy of the left common carotid artery treated only with FITC-labeled ODN (A), or with FITC-labeled ODN with HVJ-liposomes (B). A cross-section of the left common carotid artery of control rat (C) is shown 14 d after balloon injury (D), or 14 d after balloon injury with PS-E2F using the HVJ-liposome method (E), with the HVJ-liposome method and CD-E2F (F), or with the HVJ-liposome method and M-E2F (G). The average ratio of intimal/medial area of the left carotid artery in groups transfected with HVJ-liposomes containing E2F decoy is shown (H). Bars represent neointima/media ratio of common carotid arteries after balloon injury from each group of animals studied (n=10). Values represent the means±SEM with statistical significance determined as *p<0.01 compared to balloon injured arteries, #p <0.05 compared to PS-E2F treated arteries. Original magnification 100× (A and B) and 25× (C-G). The scale bar represents 200 μm.

Figure 14:
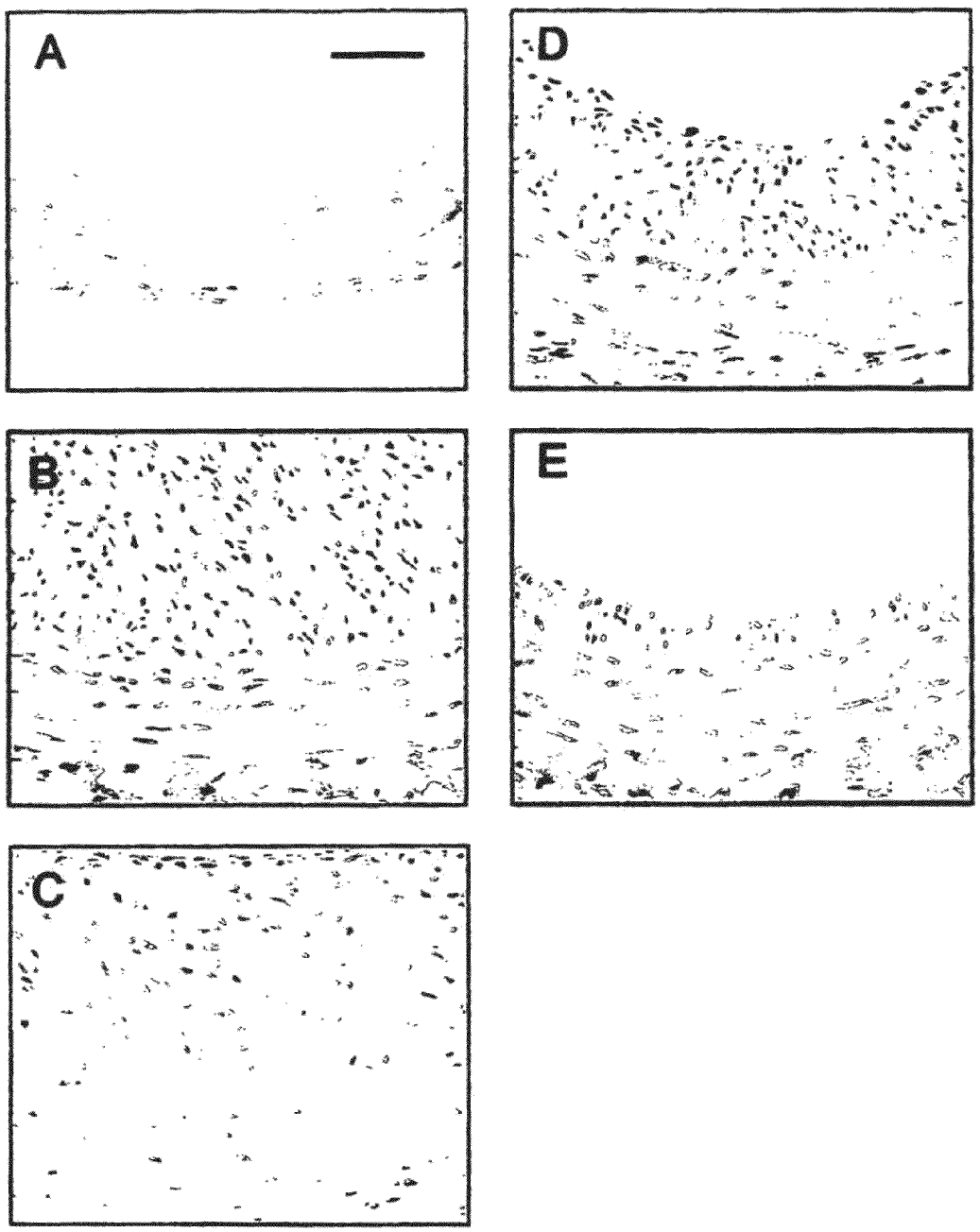

FIG. 14 shows the PCNA expression in rat carotid artery after balloon injury. PCNA staining of control vessel (A), balloon injured vessel (B), arteries with M-E2F (C), arteries with PS-E2F (D), and arteries with CD-E2F (E). PCNA positive cells appear as brownish-black. All figures are at a 200× magnification. The scale bar represents 50 μm.

BEST MODE FOR CARRYING OUT THE INVENTION

It should be understood throughout the present specification that articles for a singular form (e.g., "a", "an", "the", etc. in English; "ein", "der", "das", "die", etc. and their inflections in German; "un", "une", "la", "le", etc. in French; articles, adjectives, or any other equivalents etc. in other languages) include the concept of their plurality unless otherwise mentioned. It should be also understood that the terms as used herein have definitions commonly used in the art unless otherwise mentioned.

The practice of the present invention will employ, unless otherwise indicated, conventional methods of protein chemistry, viral immunobiology, molecular biology and recombinant DNA techniques within the skill of the art. Such techniques are explained fully in the literature. See, e.g., Sambrook, et al., Molecular Cloning: A Laboratory Manual (Cold Spring Harbor Laboratory, 1989); and F. M. Ausubel et al. Current Protocols in Molecular Biology, Greene Publishing Associates & Wiley Interscience New York.

Unless specifically stated, the terms used in the specification have the same meaning as used in the art. For convenience, certain terms employed in the specification, examples, and appended claims are collected here.

As used herein the term "animal" refers to mammals. Preferably, mammals may be primates, such as humans. Likewise, a "patient" or "subject" to be treated by the method of the invention can mean either a human or non-human animal. Preferably, such a subject or patient may be human.

As used herein the term "decoy" or "decoy compound" refers to a compound which mimics a chromosomal site to which a transcriptional factor such as AP-1 or E2F binds, or which mimics a chromosomal site of a gene controlled by a transcriptional factor such as AP-1, E2F and the like, to which the transcriptional regulatory factor binds (hereinafter referred to "target binding site"), thereby competing with the chromosomal binding site for binding to the transcriptional factor.

As used herein "dumbbell decoy" or "CDODN" refers to a circular oligonucleotide with a double-stranded stem region and two loop structures. The stem region comprises a sequence which acts as a decoy. Preferably, the CDODN is formed from the ligation of two identical stem-loop structures.

The term "$ED_{50}$" means the dose of a drug which produces 50% of its maximum response or effect. The term "$LD_{50}$" means the dose of a drug which is fatal to 50% of the population treated.

An "effective amount" of a compound (e.g. decoy) or a composition of the invention, with respect to the subject method, refers to an amount effective for treating or preventing a disease or disorder related to EF-2 or AP-1. A "therapeutically effective amount" or "pharmacologically effective amount" of a compound (e.g. decoy) or a composition of the invention, with respect to the subject method, refers to a sufficient amount for a desired pharmacological effect (e.g. ameliorating, curing or delaying the onset of a disease or disorder to be treated). The amount to be administered depends on a variety of factors including the subject to be treated or the disease or disorder to be treated, and preferably, such an amount should be optimized such that a desired effect is attained without significant adverse effects. Such an amount can be determined by those skilled in the art. An "effective amount", "therapeutically effective amount" or "pharmacologically effective amount" of a compound or composition of the invention can be determined by using $ED_{50}$ and/or $LD_{50}$. The therapeutic index is the dose ratio between a therapeutic effect and a toxic effect, and can be represented as the ratio $ED_{50}/LD_{50}$. The greater therapeutic index such a pharmaceutical composition has, the more preferable effects can be attained. For determination of $ED_{50}$ and $LD_{50}$ cell culture assays and animal experiments can be used and data obtained therefrom can be used to infer the dose range for human use. Preferably, the present invention has little or no toxic effect. Such dose varies depending on the form of administration, susceptibility of the subject, administration route, and the like.

The term "organ" refers to two or more adjacent layers of tissue, which layers of tissue maintain some form of cell-cell and/or cell-matrix interaction to form a microarchitecture. The term "tissue" refers to a group or layer of similarly specialized cells which together perform certain specialized functions.

The term "heterologous" when used with reference to a nucleic acid indicates that the nucleic acid comprises two or more subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11-17 (1988) e.g., as implemented in the program PC/GENE (Intelligenetics, Mountain View, Calif., USA).

Methods for alignment of sequences for comparison are well known in the art. Optimal alignment of sequences for comparison may be conducted by the local homology algorithm of Smith and Waterman (1981) Adv. Appl. Math. 2: 482; by the homology alignment algorithm of Needleman and Wunsch (1970) J. Mol. Biol. 48: 443; by the search for similarity method of Pearson and Lipman (1988) Proc. Natl. Acad. Sci. USA 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) Gene, 73: 237-244 and Higgins and Sharp (1989) CABIOS 5: 151-153; Corpet, et al. (1988) Nucleic Acids Research 16, 10881-90; Huang, et al. (1992) Computer Applications in the Biosciences 8, 155-65, and Pearson, et al. (1994) Methods in Molecular Biology 24, 307-31. Alignment is also often performed by inspection and manual alignment.

"Stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part 1 chapter 2 "overview of principles of hybridization and the strategy of nucleic acid probe assays", Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

The term "nucleic acid" refers to a deoxyribonucleotide or ribonucleotide polymer in either single- or double-stranded form. Unless otherwise limited, the term encompasses polymer sequences that include any of the known base analogs of DNA and RNA including, but not limited to, 4-acetylcytosine, 8-hydroxy-N6-methyladenosine, aziridinylcytoine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminoraethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurlne.

The term "gene" refers to a nucleic acid (e.g., DNA) sequence that comprises coding sequences necessary for the production of a polypeptide or precursor (e.g., c-myc). The polypeptide can be encoded by a full length coding sequence or by any portion of the coding sequence so long as the desired activity or functional properties (e.g., enzymatic activity, ligand binding, signal transduction, etc.) of the full-length polypeptide or active fragment are retained. The term also encompasses the coding region of a structural gene and including the sequences located adjacent to the coding region on both the 5' and 3' ends for a distance of about 1 kb or more on either end such that the gene corresponds to the length of the full-length mRNA. The sequences which are located 5' of the coding region and which are present on the mRNA are referred to as 51 non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA. rRNA, tRNA, or snRNA) through "transcription" of the gene into RNA (i.e., via the enzymatic action of an RNA polymerase), and for genes which encode protein, into protein through "translation" of mRNA. Gene expression can be regulated at many stages in the process. "Upregulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

DNA molecules are said to have "5' ends" and "3' ends" because mononucleotides are reacted to make oligonucleotides or polynucleotides in a manner such that the 5 phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region However, enhancer elements can exert their effect even when located 3° of the promoter element and the coding region. Transcription termination and polyadenylation signals are located 3' or downstream of the coding region.

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural environment. Isolated nucleic acid is, as such, present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA is which encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an Isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in. the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemioal assays), fluorescent, radioactive, and luminescent systems. It is not intended that the present Invention be limited to any particular detection system or label.

As used herein, the term "transcription factor" or "transcriptional factor" refers to proteins that interact with one another and RNA polymerase enzyme to modulate transcription. Transcription factors target genes by recognizing specific DNA regulatory sequences (e.g., enhancers) or other transcription factors. Transcription factors are often referred to as "trans-factors" that interact with "cis-elements" (e.g., enhancers) because they are typically produced from genes located distantly (trans) from their sites of regulation (cis). Some transcription factors are biologically active only when bound to another copy of itself (i.e., homodimers linked through "homodimerization domains") or to other transcription factors (i.e., h_t_rodimers linked through "heterodimerization domains"). For most transcription factors, specific and distinct regions of the protein mediate DNA binding (i.e., "tDNA binding domains") and transcriptional activation (i.e., "activation domains"). The most important level of gene expression regulation is exerted at the transfer process of this information from the genes into messenger RNA molecules; this process is called transcription. These proteins or transcriptional factors are classified according to their mode of action in 4 groups: general transcriptional factors, activators, coactivators and repressors. In transcriptional factors, diseases like Aniridia, Rubinstein-Taybi syndrome and Hodgkin's disease, transcriptional factor have been involved and in some, the molecular cause i.e. the mutations responsible for the molecular dysfunction in a transcriptional factor have been elucidated. The term "AP-1" refers to a transcriptional factor which binds to specific DNA sequences present in a large number of genes associated with cell proliferative response and extracellular matrix production. "E2F" refers to a transcriptional factor that was shown to be critical in the E1A-mediated activation of the Adenovirus E2 promoter. E2F is now known to be identical to the differentiation-regulated transcription factor, DRTF, which was originally described as a transcription factor down-regulated during the differentiation of F9 embryonic carcinoma cells. E2F forms a complex with cyclin A, cdk2, and pRB, activates and phosphorylates these cell cycle regulatory genes, and is critical to the process of cell growth and proliferation.

As used herein the term "a disease or disorder related to a transcriptional factor" refers to a disease or disorder associated with increased or decreased levels or an Inappropriate (enhanced, modified or impaired, etc.) function of such a transcriptional factor in the diseased cell or tissue. Preferably, such diseases include inflammatory diseases (rheumatoid arthritis, osteoarthritis etc.), dermatitis (atopic dermatitis", 'psoriasis etc.), aneurism, arteriosclerosis, atherosclerosis, angitis, restenosis after PTCA and PTA, cancer or carcinoma, asthma and the like. By using dumbbell decoys, the present invention attained significant effects over the prior art such as resistance to nuclease and significantly improved long-acting effects in cells or tissues. As used herein "a disease or disorder related to AP-1" refers to a disease or disorder associated with increased or decreased levels of AP-1 in the diseased cell or tissue, or associated with increased expression of genes activated by AP-1. Preferably, such diseases are related to inflammation and cell proliferation. More preferably, such a disease or disorder may be vascular smooth muscle cell proliferation or neointimal hyperplasia. The term "a disease or disorder related to E2F" refers to a disease or disorder associated with increase levels of E2F in the diseased cell or tissue, or associated with increase expression of genes activated by E2F. Preferably, such a disease or disorder may be vascular smooth muscle cell proliferation or neointimal hyperplasia.

The term "biologically active," as used herein, refers to a protein or other molecules which have structural, regulatory, or biochemical functions of a naturally occurring molecule (e.g., molecules having transcriptional activity, or binding affinity to a particular site of a gene).

(ii. Detailed Description of Preferred Embodiments of the Present Invention)

The present invention provides a circular dumbbell oligodeoxynucleotide (CDODN) comprising two loop structures and a stem structure, wherein the stem structure comprises a nucleotide sequence capable of binding the DNA-binding domain of a transcriptional factor. The present invention further provides a pharmaceutical composition comprising said CDODN. The pharmaceutical composition can be used for treating and/or preventing a disease or disorder related to such a transcriptional factor. The present invention also provides a method for treating and/or preventing a disease or disorder related to such a transcriptional factor, comprising administering to the subject a therapeutically effective amount of a CDODN comprising two loop structures and a stem structure, where in the stem structure comprises a nucleotide sequence capable of binding the DNA-binding domain of the transcriptional factor. The present invention achieved improved efficacy for treating and/or preventing a disease or disorder related to a transcriptional factor as compared to a conventional decoy or decoy composition, by providing a circular dumbbell decoy or decoy composition and thereby providing significantly improved stability of the decoy or decoy composition after administration to a subject.

The present invention demonstrates that transfer of novel AP-1 decoy ODN prevented VSMC proliferation in vitro and neointima formation after balloon injury in vivo. These results indicate that the transcription factor AP-1 plays an important role in proliferation of VSMC and neointima formation after balloon injury.

Accumulating evidence indicates that activation of MAP kinase cascades is a key event in the proliferation and cell growth of VSMC in response to injury (see Ohashi N, et al., Arterioscler Thromb Vasc Biol. 2000;20:2521-2526; Koyama H, et al., Circ Res. 1998;32:713-721; Hu Y, et al., Arterioscler Thromb Vasc Biol. 1997;17:2808-2816; Pyles J M, et al., Circ Res. 1997;81:904-910; and Izumi Y et al., Circ Res. 2001; 88: 1120-1126). These MAP kinases, such as JNK and ERK, control the expression and activation of AP-1 transcription factor (see Davis R J., J Biol Chem 1993;268: 14553-14556; and Seger R, et al., FASEB J. 1995;9:726-73). AP-1 binds to specific DNA sequences present in a large number of genes associated with VSMC proliferative response and extracellular matrix production (see Karin. M., J. Biol Chem. 1995;270:16483-16486; and Whitmarch A J, Davis R J, J Mol Med. 1996;74:589-607). These findings suggest that the activation of AP-1 might be an important step leading to neointima formation. However, direct demonstration of the role of AP-1 in the pathogenesis of neointima formation has been hampered by the absence of specific and potent pharmacologic inhibitors of AP-1. In order to test the hypothesis that AP-1 plays a critical role in the pathogenesis of VSMC proliferation and neointima formation, we used a new AP-1 ODN transfection approach. The transfection of double-stranded cis element decoy ODN results in the removal of all trans-factors from the endogenous cis-element of the same sequence with a subsequent inhibition of the gene expression. Thus, the present invention is the first to directly demonstrate the involvement of AP-1 in VSMC proliferation and neointima formation.

In this invention, we used high glucose and serum as stimulants to enhance VSMC proliferation and migration. These stimulants induce many early genes, growth factors, and mitogens through the MAPK pathway (see Miano J M, et al., Arterioscler Thromb. 1993;13:211-219; Bennett M R. et al. J Clin Invest. 1994;93:820-828; Briata P, et al., Biochem Biophys Res Commun. 1989:165:1123-1129; Inaba T, et al. Diabetes 1996;45:507-512; Di Paolo S, et al., Am J Pathol. 1996; 149:2095-2106; Schwartz S M, et al., Circ. Res. 1995;77: 445-465; Lindner V, et al. Circ Res. 1991;68:106-113). The present invention also demonstrates that high glucose and serum stimulate endogenous expression of cell cycle-regulatory genes cyclin A and PCNA, which are required for cell cycle progression from the G1 phase to the S phase. AP-1 ODN effectively abolished proliferation, migration and cyclin A and PCNA gene expression of VSMC induced by high glucose and serum. Furthermore, our data using cyclin A promoter serial deletion or mutation constructs showed that the ATF (activating transcription factor) site, which is responsible for binding of a transcriptional factor such as AP-1 protein, mediates up-regulation of cyclin A gene expression by high glucose. Transfection of AP-1 decoy ODN with the luciferase reporter constructs, but not mismatched ODN, also completely abolished luciferase expression of cyclin A induced by high glucose and serum. These observations, taken together with the In vitro results that transfection with the AP-1 decoy inhibited VSMC proliferation and migration, demonstrated that the suppression of VSMC growth and VSMC migration were involved in the inhibition of neointima formation by the AP-1 decoy.

To transfect AP-1 decoy ODN into rat carotid artery, we used the HVJ-liposome technique, which is a very effective method in gene transfer into medial VSMC of intact arteries not subjected to endothelial denudation. Transfection of FITC-labeled ODN by HVJ-liposome method resulted in strong fluorescence, readily detected in all layers of artery. The present invention also demonstrates that AP-1 ODN effectively prevents neointima formation after balloon injury. Of interest is the finding that pre-treatment with decoy ODN was more effective than post-treatment. This finding can be explained by the time course of AP-1 activation in the injured artery. Previous studies reported that ERK and JNK activities in the vessel wall rapidly increase and reach a plateau at 5 min after injury and are maintained for 1 h after balloon angioplasty. The expression of immediate early genes, c-jun and c-fos, reaches a peak at 30 min after balloon injury. Our results also show that AP-1 activity is noted at 30 min and reaches maximum at 3 h after balloon injury. These data indicate that signal transduction in response to balloon injury is rapid, and the time of blocking is important to block the flow of signals caused by balloon injury.

Of note in our invention is that AP-1 circular dumbbell decoy ODN (CDODN) was more stable and effective than chemically modified decoy ODN. The CDODN contains two binding sites of AP-1 in a single decoy molecule without an open end, allowing multiple targeting of more than one promoter site. In previous studies, modified ODN such as phosphorothioate and methylphosphonate were widely utilized to augment stability against nucleases (see Khaled A R. et al., Clin. Immunol Immunopathol 1998; 86:170-179; Larrouy B, et al., Gene 1992; 121:189-194). These modified ODN against c-myb, c-myc, cdc2 and cdk2 as antisense, or NF-KB and E2F as decoy decreased intimal thickening in experimental restenosis (see Simons N et al, J. Clin Invest 1994; 93:1458-1464, Morishita R at al 1993 supra, Morishita R et al 1994 supra, Morishita R et al 1997 supra). However, these modified ODNs exhibit problems such as insensitivity to RNaseH, possible recycling of hydrolyzed modified nucleotides into genomic DNA, lack of sequence-specific binding effects, and immune activation. In accordance with recent reports (see Chu B C F, et al., Nucleic Acids Res. 1992; 20:5857-5858; and Abe T. et al., FEBS Lett. 1998; 425:91-96), CDODN was more stable than PSODN in the presence of serum, exonuclease III and S1 nuclease. In order to evaluate the sequence-specificity of CDODN and PSODN containing the binding sites for AP-1, we set up an in vitro competition assay. When the non-labeled CDODN and PSODN were used as competitors, both CDODN and PSODN completely inhibited the AP-1 binding to labeled probe, but the sequence-specificity of CDODN was about 10 times greater than the effect of PSODN. Further, we evaluated the inhibitory effect of CDODN and PSODN on AP-1 binding activity induced by high glucose or serum in VSMC. Both CDODN and PSODN significantly attenuated the AP-1 binding activity but the inhibitory effect of CDODN was greater. These results show that CDODN has more affinity for the AP-1 binding protein than PSODN.

In accordance with these in vitro data, CDODN was more effective in preventing neointima formation after vascular injury. An additional potential merit of dumbbell decoy ODN is lack of mutational potential, due to introduction into genomic DNA during DNA replication or repair upon recycling of hydrolyzed modified nucleotides.

In conclusion, the present invention demonstrated that dumbbell decoy ODN have the markedly enhanced stability as compared to the previously attempted modified ODN. Moreover, the inhibition of AP-1 activity by decoy ODN effectively decreased cell proliferation and migration in vitro as well as neointima formation in vivo. The present invention provides a new potential therapeutic strategy for the treatment of restenosis by employing CDODN with minimized side effects and highly effective HVJ-liposome gene delivery technique.

In another aspect of the invention, the present invention provides a novel E2F-decoy. Several studies demonstrated that inhibition of cell-cycle regulatory genes successfully blocked VSMC proliferation and neointima formation in injured vessels. Inhibition of a single cell-cycle regulatory gene, however, is insufficient to prevent VSMC proliferation and neointima formation. We therefore focused on the transcription factor E2F, which is associated with up-regulated expression of various genes involved in G1/S cell-cycle progression, including PCNA, c-myc, c-myb, cdc2, and cdk2 (see Bielinska A, et al. 1990 supra; Chu B C F, Orgal. L., Nucleic Acids Res. 1992; 20:5857-5858; and Abe T, et al., FEBS Lett. 1998; 425:91-96). In this invention, we demonstrate that the transfection of E2F decoy successfully blocked smooth muscle cell proliferation and neointimal hyperplasia in injured vessels, consistent with previous in vitro and in vivo studies.

In the present invention, we devised a novel circular dumbbell decoy to improve stability against nucleases. In previous studies, modification of ODN with phosphorothioate, methylphosphonate, or other foreign materials have been used to augment stability against nucleases (see Tanaka H. et al., Nucleic Acids Res 1994; 22: 3069-3074; Bielinska A, at al. 1990 supra). Although the stability of ODN against nucleases was enhanced by chemical modification, these modified ODN could induce other different problems because of the employment of foreign materials to modify ODN. Recently, dumbbell type ODN has been reported to increase nuclease resistance and uptake into cells as compared to the chemically modified linear ODN (see Chu B C, et al., Nucleic Acids Res 1992; 20: 5857-5858; Abe T et al., FEBS Lett 1998; 425: 91-96). We therefore designed a novel circular dumbbell decoy ODN for E2F binding site. Our CD-E2F contains two binding sites of E2F in a single decoy molecule without an open end, allowing multiple targeting of a target promoter site or targeting more an one promoter site. As expected, the CD-E2F was more stable than PS-E2F in the presence of the nucleases and serum. In addition, the sequence-specificity of CD-E2F, assessed by in vitro competitive binding assay, was nearly 10 times greater than that of PS-E2F. Furthermore, the inhibitory effect of CD-E2F on glucose- and serum-induced E2F binding activity in VSMCs was also greater than that of PS-E2F. These results indicate that CD-E2F has an enhanced stability and excellent sequence-specific inhibitory effect on E2F binding site.

Poor cellular uptake and subsequent lysosomal degradation after endocytosis of ODN delivered by conventional liposome methods have been the major obstacles for ODN therapy (see Marcus-Sekure C J., Anal Biochem 1988; 172: 289-795; Stein C A, Cohen J S., Cancer Res 1988; 48: 2659-2668). In order to overcome this obstacle, we used the HVJ-liposome technique to transfect E2F decoy into rat carotid artery. In this delivery system, exogenous molecules such as plasmid DNA or ODN are enveloped in liposomes that comprise phospholipids and cholesterol. The liposomes are then fused with UV-inactivated HVJ to form HVJ-liposomes. Fusion proteins from HVJ promote fusion of the liposomes with the cell membranes and deposition of molecules into the cell. We recently reported that transfection of a FITC-labeled decoy using the HVJ-liposome method into cultured human VSMC was very effective in gene transfer than conventional transfection method (see Ahn J D et al., Diabetologia 2001; 44: 713-720). In accordance with this, transfection of FITC-labeled decoy by the HVJ-liposome method in vivo resulted in a strong fluorescence, readily detected in all layers of the artery.

Although hyperglycemia has been suggested to contribute to the development of macrovascular complications in patients with diabetes, few studies have focused on the direct effect of elevated glucose concentrations on VSMCs (Ahn J D et al., 2001 supra; Natarajan R et al., Hypertension 1999; 33: 378-384; Yasunari K et al., Circ Res 1997; 81: 953-962). In our invention, we examined the effect of high concentration of glucose on B2F DNA-binding activity in VSMCs as well as cell cycle regulatory genes, and proliferation of VSMCs. Our studies show that E2F DNA-binding activity and luciferase activity of the [E2F]×4-luciferase construct, which contains four E2F binding sites in the promoter region, were significantly increased after treatment of high concentration of glucose in VSMCs. These effects were additive with serum. The present invention also demonstrates that high glucose and serum stimulate the endogenous expression of cell cycle-regulatory genes such as cyclin A and PCNA, which are important for cell cycle progression from Gl to the S phase. Transfection of E2F decoy, but not a mismatched sequence oligonucleotide (M-E2F), effectively attenuated VSMC proliferation as well as expression of PCNA and cyclin A genes induced by high glucose and serum, consistent with the results of promoter study of cyclin A. Furthermore, our results, derived from the use of cyclin A promoter serial deletions or mutation constructs, demonstrate that the glucose-stimulated up-regulation of cyclin A gene expression is mediated by the E2F site in cyclin A promoter. Co-transfection of E2F decoy, but not M-E2F, with the luciferase reporter constructs also completely abolished luciferase expression under the cyclin A promoter induced by high glucose.

Finally, transfection of CD-E2F prevented neointima formation after balloon injury more effectively than PS-E2F. Cells positive for PCNA staining in vessels treated with CD-E2F also were found to be much less than in PS-E2F treated vessels or untransfected vessels. These observations, taken together with the vitro results, indicate that CD-E2 is more effective in suppression of VSMC growth and in preventing neointima formation following vascular injury. An additional potential therapeutic benefit of CD-E2F is its lack of mutational potential, whereas ODN modified with foreign materials could have mutational potential when hydrolyzed nucleotides are recycled and introduced into genomic DNA during DNA replication.

In conclusion, the present invention demonstrates that CD-E2F has a markedly enhanced stability and an excellent sequence-specific decoy effect compared to conventional modified ODN. Moreover, inhibition of the DNA binding activity of E2F using CD-E2F significantly decreased cell cycle regulatory gene expression and cell proliferation in vitro as well as in vivo. The present invention employing a novel CD-E2F and a highly effective HVJ-liposome delivery technique will provide a new therapeutic strategy to prevent restenosis following angioplasty in humans with minimal side effects.

In a preferred embodiment of the invention, the present invention, therefore, provides pharmaceutical compositions comprising an AP-1 and alternatively or additionally an E2F decoy as an active ingredient and optionally another transcriptional factor (e.g. NFκB) decoy, for the therapy and prophylaxis of various AP-1- or E2F-associated diseases and a method for said therapy and prophylaxis.

The diseases in which the therapeutic/prophylactic composition of the invention is indicated are AP-1 and also E2F-associated diseases, that is to say diseases caused by the unwanted activation of genes under the control of the transcriptional regulatory factor AP-1 or E2F, preferably such diseases comprises but are not limited to inflammatory diseases (rheumatoid arthritis, osteoarthritis etc.), dermatitis (atopic dermatitis, psoriasis etc.), aneurism, arteriosclerosis, atherosclerosis, angitis, restenosis after PTCA and PTA, cancer or carcinoma, asthma and the like.

AP-1 is a key regulator of various important genes, including those that involve the production of enzymes that cause tissue destruction, (ii) cytokines associated with chronic inflammation, and (iii) proteins necessary for cell proliferation. Therefore, the AP-1 dumbbell decoy may be a potentially powerful agent in treating chronic inflammatory diseases.

The E2F family of transcription factors plays an important role in the regulation of cell proliferation. Therefore the novel E2F decoy provided by the present invention may be a potentially powerful agent in treating diseases associated with abnormal cell proliferation.

In another embodiment of the invention, the diseases for which the therapeutic/prophylactic composition of the invention is indicated are NF-κB-associated diseases, that is to say diseases caused by the unwanted activation of genes under control of the transcriptional regulatory factor NF-κB, and among such diseases can be reckoned ischemic diseases, inflammatory diseases, autoimmune diseases, cancer metastasis and invasion, and cachexia. The ischemic disease includes ischemic diseases of organs (e.g. ischemic heart diseases such as myocardial infarction, acute heart failure, chronic heart failure, etc., ischemic brain diseases such as cerebral infarction, and ischemic lung diseases such as pulmonary infarction), aggravation of the prognosis of organ transplantation or organ surgery (e.g. aggravation of the prognosis of heart transplantation, cardiac surgery, kidney transplantation, renal surgery, liver transplantation, hepatic surgery, bone marrow transplantation, skin grafting, corneal transplantation, and lung transplantation), reperfusion disorders, and post-PTCA restenosis. The inflammatory disease mentioned above includes various inflammatory diseases such as nephritis, hepatitis, arthritis, etc., acute renal failure, chronic renal failure, and arteriosclerosis, among other diseases. The autoimmune disease mentioned above includes but is not limited to rheumatism, multiple sclerosis, and Hashimoto's thyroiditis. Particularly the pharmaceutical composition containing the NF-κB decoy according to the present invention as an active ingredient is very suited for the therapy and prophylaxis of reperfusion disorders in ischemic diseases, aggravation of the prognosis of organ transplantation or organ surgery. post-PTCA restenosis, cancer metastasis and invasion, and cachexia such as weight loss following the onset of a cancer.

Any other diseases in which a transcriptional factor is associated can be treated or prevented by the decoy of the invention. Such diseases include but not limited to: E2F-related diseases, disorders or conditions such as neointimal hyperplasia, neoplasia, glomerulonephritis, angiogenesis, inflammation; AP-I-related diseases, disorders or conditions such as neointimal hyperplasia, cardiac myocyte growth/differentiation; NFκB-related diseases, disorders or conditions such as inflammation, immune response, transplant rejection, ischemia-reperfusion injury, glomerulonephritis, inflammatory bowel diseases; SSRE-related diseases, disorders or conditions such as neointimal hyperplasia, bypass grafts, angiogenesis, collateral formation; CREB-related diseases, disorders or conditions such as cAMP activated events; MEF-2-related diseases, disorders or conditions such as cardiac myocyte differentiation and growth; CArG box-related diseases, disorders or conditions such as cardiac myocyte growth and differentiation; tax-related diseases, disorders or conditions such as HTLV infection; VP16-related diseases, disorders or conditions such as Herpes infection; TAR/tat-related diseases, disorders or conditions such as HIV infection; GRE/HRE MRE-related diseases, disorders or conditions such as steroid hormone processes (breast or prostate cell growth); H at shock RE-related diseases, disorders or conditions such as cellular stresses e.g. ischemia hypoxia; SRE-related diseases, disorders or conditions such as cell proliferation/differentiation; AP-2-related diseases, disorders or conditions such as cell proliferation; sterol response element-related diseases, disorders or conditions such as hypercholesterolemia; TRE (TGFb responsive element)-related diseases, disorders or conditions such as cell growth, differentiation, migration, angiogenesis, intimal responsive hyperplasia, matrix generation, element apoptosis.

Particularly, the pharmaceutical composition containing the decoy according to the present invention as an active ingredient is highly suitable for the therapy and prophylaxis of reperfusion disorders in ischemic diseases, aggravation of the prognosis of organ transplantation or organ surgery, post-PTCA restenosis, cancer metastasis and invasion, and cachexia such as weight loss following the onset of cancer.

The decoy that can be used in the present invention may be any compound that specifically antagonizes the binding site of the chromosome corresponding to the type of the transcriptional factor and includes but is not limited to nucleic acids and their analogs. As preferred examples of said decoy, there can be mentioned oligonucleotides containing the nucleotide sequence of TGACTCA (AP-1) and TTTCGCGC (E2F) (the sequences from the 7th through the 13th nucleotides from the 5'-end, and the 8th through the 15th nucleotides from the 5'-end of SEQ ID NO:1 and 2, respectively, in Sequence Listing), GGGATTTC (NFκB) or its complementary sequence, muteins thereof, and compounds containing any of the above oligonucleotide sequences. The oligonucleotides may be DNAs or RNAs, and may contain modified nucleotides and/or pseudonucleotides. Furthermore, those oligonucleotides, variants thereof, or compounds containing any of them may be single-stranded or double-stranded and linear or cyclic. Variants are those nucleic acid sequences with mutations such as substitution, addition and/or deletion of any part of the above-mentioned sequence, which specifically antagonize the chromosomal binding sites to which a transcriptional factor are conjugated. The more preferred decoy includes double-stranded oligonucleotides each containing one or a plurality of the above nucleotide sequences and variants thereof. Oligonucleotides which can be used in the present invention include oligonucleotides modified so as to be less susceptible to biodegradation, such as those oligonucleotides containing the thiophosphoric diester bond available upon substitution of sulfur for the oxygen of the phosphoric diester moiety (S-oligo) and those oligonucleotides available upon substitution of a methyl phosphate group carrying no electric charge for the phosphoric diester moiety.

Regarding the technology for producing the decoy for use in the present invention, conventional chemical or biochemical synthesis methods can be utilized. When a nucleic acid, for instance, is to be used as the decoy, methods for nucleic acid synthesis which are commonly used in genetic engineering can be employed. For example, the object decoy oligonucleotide can be directly synthesized on a DNA synthesizer. Or a nucleic acid or its fragments, each synthesized beforehand, can be amplified by PCR or using a cloning vector or the like. Furthermore, the desired nucleic acid can be obtained by such procedures as cleavage with restriction enzymes or the like and/or ligation by means of DNA ligase or the like. In order to obtain a decoy nucleotide which is more stable within cells, the base, sugar or/and phosphoric acid moieties of the nucleic acid may be alkylated, acylated, or otherwise chemically modified.

The pharmaceutical composition containing the decoy as an active ingredient according to the present invention is not limited in form as long as the active ingredient may be taken up by the cells in the affected site or the cells of the target tissue. Thus, the decoy, either alone or in admixture with the common pharmaceutical carrier, can be administered orally, parenterally, topically or externally.

The pharmaceutical compositions may be provided in liquid dosage forms such as solutions, suspensions, syrups, liposomes, lotions, etc. or in solid dosage forms such as tablets, granules, powders, and capsules. Where necessary, those pharmaceutical compositions may be supplemented with various vehicles, excipients, stabilizers, lubricants, and/or other conventional pharmaceutical additives, such as lactose, citric acid, tartaric acid, stearic acid, magnesium stearate, terra alba, sucrose, corn starch, talc, gelatin, agar, pectin, peanut oil, olive oil, cacao butter, ethylene glycol, and so on.

Particularly when a nucleic acid or a modification product thereof is used as the decoy, the preferred dosage form includes those which are generally used in gene therapy, such as liposomes including but not limited to membrane fusion liposomes utilizing Sendai virus and liposomes utilizing endocytosis, preparations containing cationic lipids such as Lipofectamine (Life Tech Oriental) or virosomes utilizing a retroviral vector, adenoviral vector, or the like. Particularly preferred are membrane fusion liposomes.

The structure of such a liposomal preparation may be any of a large unilamellar vesicle (LUV), a multi-lamellar vesicle (MLV), and a small unilamellar vesicle (SUV). The approximate size of vesicles may range from 200 to 1000 nm for LUV, from 400 to 3500 nm for MLV, and from 20 to 50 nm for SUV but in the case of a membrane fusion liposomal preparation using Sendai virus, for instance, MLV with a vesicular system of 200-1000 nm in diameter is preferably employed.

There is no limitation the technology for liposome production as long as the decoy can be successfully entrapped in vesicles. Thus, such liposomes can be manufactured by conventional techniques such as the reversed phase evaporation method (Szoka, F., et al; Biochira. Biophys. Acta, Vol. 601 559 (1980)), ether injection method (Deamer, D. W.: Ann. N. Y. Acad. Sci., Vol. 303 250 (1978)), and surfactant method (Brunner, J., et al; Biochim. Biophys. Acta, Vol. 455 322 (1976)), to name but a few examples.

Lipids that can be used for forming the liposomes include phospholipids, cholesterol and its derivatives, and nitrogen-containing lipids but phospholipids are generally preferred. Phospholipids that can be used include naturally-occurring phospholipids such as phosphatidylcholine, phosphatidylserine, phosphatidylglycerol, phosphatidylinositol, phosphatidylethanola mine, phosphatidic acid, cardiolipin, sphingomyelin, egg yolk lecithin, soybean lecithin, lysolecithin, etc., the corresponding phospholipids hydrogenated by the conventional method, and synthetic phospholipids such as dicetyl phosphate, distearoylphosphatidylcholine, dipalmitoylphoshatidylcholine, dipalmitoylphosphatidylethanolamine, dipalmitoylphosphatidylserine, oleostearoylphosphatidylcholine, oleostearoylphosphatidylethanolamine, oleostearoylphosphatidylserine, and so on.

The lipids, particularly phospholipids, can be used individually or in a suitable combination. By using a lipid containing a positively-charged group such as ethanolamine or choline, the binding of an electrically negative decoy nucleotide can be enhanced. In addition to the principal phospholipid, various compounds such as cholesterol and its derivatives, stearylamine, tocopherol, etc., which are known as liposome additives, can be added in the manufacture of liposomes.

To the resulting liposomes can be added a membrane fusion promoter such as Sendai virus, inactivated Sendai virus, a membrane fusion promoting protein purified from Sendai virus, polyethylene glycol, or the like, for assisting in the intracellular uptake by the cells at the affected site or of the target tissue.

A typical procedure for the production of pharmaceutical liposomes is now described in detail. The above-mentioned liposome-forming substance as well as cholesterol or the like is dissolved in an organic solvent such as tetrahydrofuran, chloroform, ethanol, or the like. In a suitable vessel, the solvent is distilled off under reduced pressure to leave a film of the liposome-forming substance on the inside wall of the vessel. Then, a buffer containing the decoy is added and the mixture is stirred. After optional addition of said membrane fusion promoter, the liposomes are isolated. The liposomes in which the decoy has thus been entrapped are suspended in a suitable medium or a lyophilizate thereof is redispersed in a suitable medium for use in therapy. The membrane fusion promoter may be added in the interim period after isolation of the liposomes and b fore use.

There is no limitation On the decoy content of the pharmaceutical composition containing the decoy as an active ingredient as long as the decoy is contained in amounts effective to control a transcriptional factor-associated diseases. Thus, the decoy content can be liberally selected according to the disease to be controlled, the target site, dosage form, and dosage schedule.

The pharmaceutical composition containing the decoy as an active ingredient as provided in the above manner can be administered by various methods according to the type of disease and the kind of decoy contained. Taking ischemic diseases, inflammatory diseases, autoimmune diseases, cancer metastasis or invasion, and cachexia as examples, the composition can be infused intravascularly, applied directly to the affected area, injected into the lesion, or administered into the regional blood vessels in the affected region. As a further specific example, when PTCA is performed for treatment of infarction of an organ, the pharmaceutical composition can be administered into the local blood vessel concurrently with the operation or pre-and postoperatively. For organ transplantation, the graft material can be previously treated with the composition of the invention. Furthermore, in the treatment of osteoarthritis or rheumatism, the composition can b directly injected into the joint.

The dosage of the decoy is selected with reference to the patient's age and other factors, type of disease, the kind of decoy used etc. but for intravascular, intramuscular, or intraarticular administration, for instance, a unit dose of 10-10,000 nmoles can generally be administered once to a few times daily.

The following examples are offered by way of illustration and not by way of limitation.

EXAMPLES

Example 1

Inhibitory Effects of Novel AP-1 Decoy Oligodeoxynucleotides on Proliferation of Vascular Smooth Muscle Cells in vitro and Neointima Formation in vivo Materials and Methods
Animals Nine- to ten-week old male Sprague-Dawley rats (Hyochang, Taegu, Korea) weighing 280 to 320 g were used. All procedures were in accordance with institutional guidelines for animal research.
Cell Culture Human VSMC were harvested as described in Ahn et al 2001 supra, and rat aortic smooth muscle cells were harvested from the thoracic aorta of adult male Sprague-Dawley rats (200-250 q). VSMC were cultured in Dulbecco's modified. Eagle's medium (DMEM; Gibco BRL, Grand Island, N.Y., USA) containing 20% fetal bovine serum (Gibco BRL). VSMC purity was characterized by positive staining with smooth muscle specific α-actin monoclonal antibodies (Sigma, St. Louis, Mo., USA).
Construction of CDODN The sequences of dumbbell type and phosphorothioate double-stranded ODN derived from the AP-1 binding site and mismatched ODN used in this invention are as follows:

```
CDODN (consensus sequences are underlined),
                                         (SEQ ID NO: 3)
5'-GGATCCATGACTCAGAAGACGACACACGTCTTCTGAGTCAT-3';

phosphorothioate linear AP-1 decoy ODN (PSODN),
                                         (SEQ ID NO: 4)
5'-AGCTTGTGACTCAGAAGCT-3';

mismatched AP-1 decoy ODN (MODN),
                                         (SEQ ID NO: 5)
5'-GGATCCAAATCTCAGAAGACGACACACGTCTTCTGAGATTT-3'.
```

Figure 1:
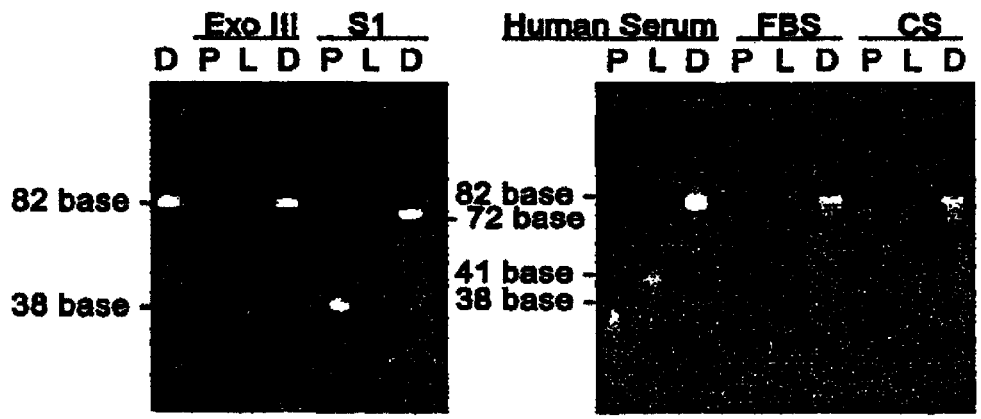
FIG. 1. shows the structure and molecular stability of AP-1 decoy ODNs. The structure of AP-1 decoy ODNs: PSODN (SEQ ID NO: 4 and SEQ ID NO: 23), Annealed form, (SEQ ID NO: 21), CDODN (SEQ ID NO: 25) and MODN (SEQ ID NO: 22). The CDODN molecule is produced from two covalently ligated identical stem-loop molecules. The CDODN, therefore, comprises two binding sites for AP-1 in its stem region. Stability test of decoy ODNs in the presence of exonuclease III (left panel), SI nuclease (left panel), or serum (right panel). Exo III; decoy ODNs treated with exonuclease III, SI; decoy ODNs treated with SI nuclease, FBS; fetal bovine serum, CS; calf serum, D; CDODN, P; PSODN, L; annealed form of CDODN before ligation.

The 5 terminus of the stem has 6 bases of a single-stranded sequence of 5'-GGATCC-3' as restriction site for BamHI. Two oligo molecules were joined by the complementary 6 base sequences at both 5' ends. ODN were annealed for 2 h, while the temperature descended from 80° C. to 25° C. One unit of T4 DNA ligase was added and incubated for 24 h at 16° C. to generate a covalently ligated dumbbell decoy ODN molecule (CDODN). The CDODN consists of two loops and one stem, which contains two AP-1 consensus sequences in tandem (FIG. 1A).
Stability of CDODN To test the stability of CDODN, 1 μg each of the non-ligated phosphodiester ODN, PSODN and CDODN were incubated with human serum, fetal bovine serum, fetal calf serum, exonuclease III or S1 nuclease. All serums were used without heat inactivation to preserve DNase activity. Each serum was added to ODN to 50% in a 100 μl reaction volume and incubated for 24 h at 37° C. Exonuclease III (Takara, Otsu, Japan) at 160 units/μg ODN was added to ODN and incubated for 2 h at 37° C. S1 nuclease (Takara) at 10 units/μg ODN was added to ODN and incubated for 30 min at 25° C. ODNs were then extracted with phenol and chloroform and examined on a 15% denaturing polyacrylamdde gel.

Effect of AP-1 Decoy ODN on Growth of VSMC

VSMC were seeded onto 96-well tissue culture plates. At 30% confluence, VSMC were rendered quiescent by incubation for 24 hours in defined serum-free medium. Then, Lipofectin containing 100 nmol/L of decoy ODN was added to the wells. The cells were incubated at 37° C. for 5 h. After 2-3 days, an index of cell proliferation was determined with the use of a WST cell counting kit (Wako, Osaka, Japan).
Cell Migration Assays VSMC migration was assessed using modified Boyden chambers (Corning, N.Y., USA). VSMC ($2 \times 10^5$ cells/well) suspended in control medium were added to the upper chamber, and tested samples were placed in the bottom chamber. After 24 hours of incubation at 37° C., cells were fixed and stained with hematoxylin and eosin. The average number of cells from 4 randomly chosen high-power (×400) fields on the lower surface of the filter was counted.
Electrophoretic Mobility Shift Assay (EMSA)

Nuclear extracts were prepared from VSMC, as described in Ahn J D at al, supra. In brief, the DNA probes such as AP-1 and mismatched decoy ODN were labeled as primers. The protein-DNA binding reaction was performed at room temperature for 20 min in a volume of 20 μl. The reaction mixture contained 6 μg of nuclear extract, 100 μg/ml poly dI:dC, 10 mmol/1 Tris/HCl (pH 7.5), 50 mmol/1 NaCl, 0.5 mmol/1 EDTA, 0.5 mmol/1 DTT, 1 mmol/1 $MgCl_2$, 4% glycerol and 60,000 cpm $^{32}$P-labeled primer DNA. After incubation, the samples were loaded onto 4% native polyacrylamide gels in 0.5× Tris-borate-EDTA buffer and were run at 150 V for 2 h. The gels were dried and visualized by autoradiography. For competition studies, the experimental conditions were identical, except that the appropriate competitor ODN were added at 50- to 100-fold molar excess to the reaction mixture before the addition of nuclear extract.
Luciferase Assay The AP-1 luciferase construct, pAP1(PMA)-TA-Luc, was purchased from Clontech and a cyclin A promoter luciferase construct was kindly provided by Dr. Masao Yoshizumi (University of Tokyo Hospital, Tokyo, Japan) (see Yoshizumi M et al J Biol Chem, 1997; 272:22259-22264). To analyze the luciferase expression, the cells were washed twice with PBS and were lysed with 200 μl of 1× Reporter lysis buffer (Promega, Madison, Wis., USA). Fifty microliters of each lysate was examined for luciferase activity.
Northern Blot Analysis Gene expression of PCNA and cyclin A was measured by northern blotting. For northern blot analysis, 10 μg of total RNA was applied to 1% formaldehyde-agarose gel and transferred to a nylon membrane. The nylon membrane was hybridized in Express Hyb™ solution at 65 ° C. for 2 h with radiolabeled PCNA cDNA probe or cyclin A cDNA probe (donated by Dr Young-Chae Chang, Dankook University Medical School, Korea), and washed according to the manufacturer's instructions. The membrane was exposed to X-ray film and the mRNA expression was quantified with densitometric analysis.
Preparation of Hemagglutinating Virus of Japan (HVJ)-Liposomes HVJ-AVE Liposomes were prepared as described in Ann J D et al, 2001 supra. Briefly, cholesterol, dioleoyl-phosphatidylethanolamine, phosphatidylcholine, sphingomyelin and phosphatidylserine were mixed in a molar ratio of 50:13.3:13.3:13.3:10. The lipid mixture was deposited on the sides of a flask by removal of chloroform. Dried lipid was hydrated in 200 μl balanced salt solution (BSS; 137 mmol/1 NaCl, 5.4 mmol/l KCl, 10 mmol/l Tris-HCl, pH 7.6) containing ODN.

Liposomes were prepared by shaking and filtration. Purified HVJ (Z strain) was inactivated by UV irradiation for 3 min just before use. The liposome suspension was mixed with HVJ in a total volume of 2 ml BSS. The mixture was incubated at 4° C. for 5 min and then for 30 min with gentle shaking at 37° C. Free HVJ was removed from the HVJ-liposomes by the sucrose density gradient centrifugation. The top layer of the sucrose gradient was collected for use.

Balloon Injury and in Vivo Gene Transfer

A 2 French Fogarty catheter was used to induce vascular injury in male Sprague-Dawley rats (280-320 g). These rats were anesthetized with pentobarbital, and the left common carotid artery was surgically exposed. A cannula was introduced into the common carotid artery via the external carotid artery. Vascular injury of the common carotid artery was induced by the passage and inflation of a balloon catheter through an arteriotomy in the external carotid artery three times. The injured segment was transiently isolated by temporary ligatures. After balloon injury, 20 µl of HVJ-liposome containing either CDODN, MODN, FITC-labeled PSODN or HVJ-liposome alone was incubated within the lumen for 10 min at room temperature. After a 10-min incubation, the infusion cannula was removed. After the transfection, blood flow to the common carotid was restored by release of the ligatures, and the wound was then closed. No adverse neurological or vascular effects were observed in any animal undergoing this procedure.

Histological Analysis

At 2 wk after transfection, rats were sacrificed and vessels were perfusion fixed with 4% paraformaldehyde, Neointima size was quantified by morphometry by individuals who were blinded to the identity of the samples. Intimal and medial areas were measured on a digitizing system (model INTUOS 6x8, Wacom, Vancouver, Wash., USA). In the case of FITC-labeled AP-1 decoy ODN transfection, the vessels were harvested at 3 d after transfection and perfusion fixed with 4% paraformaldehyde. Sections were examined by fluorescence microscopy. For immunohistochemistry, sections were incubated with rabbit anti-proliferating cell nuclear antigen antibody (1:200 dilution, SantaCruz Biotechnology, Santa Cruz, Calif., USA) and processed for immunohistochemistry in a standard manner.

Statistical Analysis

Results are expressed as mean±SEM. Analysis of variance with subsequent Duncan's test was used to determine the significance of differences in multiple comparisons. $P<0.05$ was considered statistically significant. All experiments were carried out at least three times.

Results

Construction of Dumbbell Type AP-1 Decoy with Enhanced Stability

To investigate the stability of various decoy ODN, we initially examined the molecular stability against nucleases. CDODN was stable to exonuclease III, but both PSODN and annealed decoy ODN war completely degraded after 2 h of incubation with exonuclease III (FIG. 1B). We further examined the molecular characteristics of CDODN using S1 nuclease, which digests single-stranded regions in DNA molecules. The stem regions of both the dumbbell decoy (72 bases) and PSODN (38 bases) were found to be protected from S1 nuclease, but not that of the annealed type decoy ODN (FIG. 1B).

Both PSODN and annealed decoy ODN were significantly hydrolyzed after 24 h of incubation in the presence of non-inactivated human serum, fetal bovine serum and fetal calf serum. CDODN, however, remained largely intact after 24 h of incubation with these different serums, exhibiting much improved stability when compared to both PSODN and annealed type decoy ODN (FIG. 1B).

Specific Binding of the AP-1 to Dumbbell Decoy ODN with the AP-1 Target Site

Figure 2:
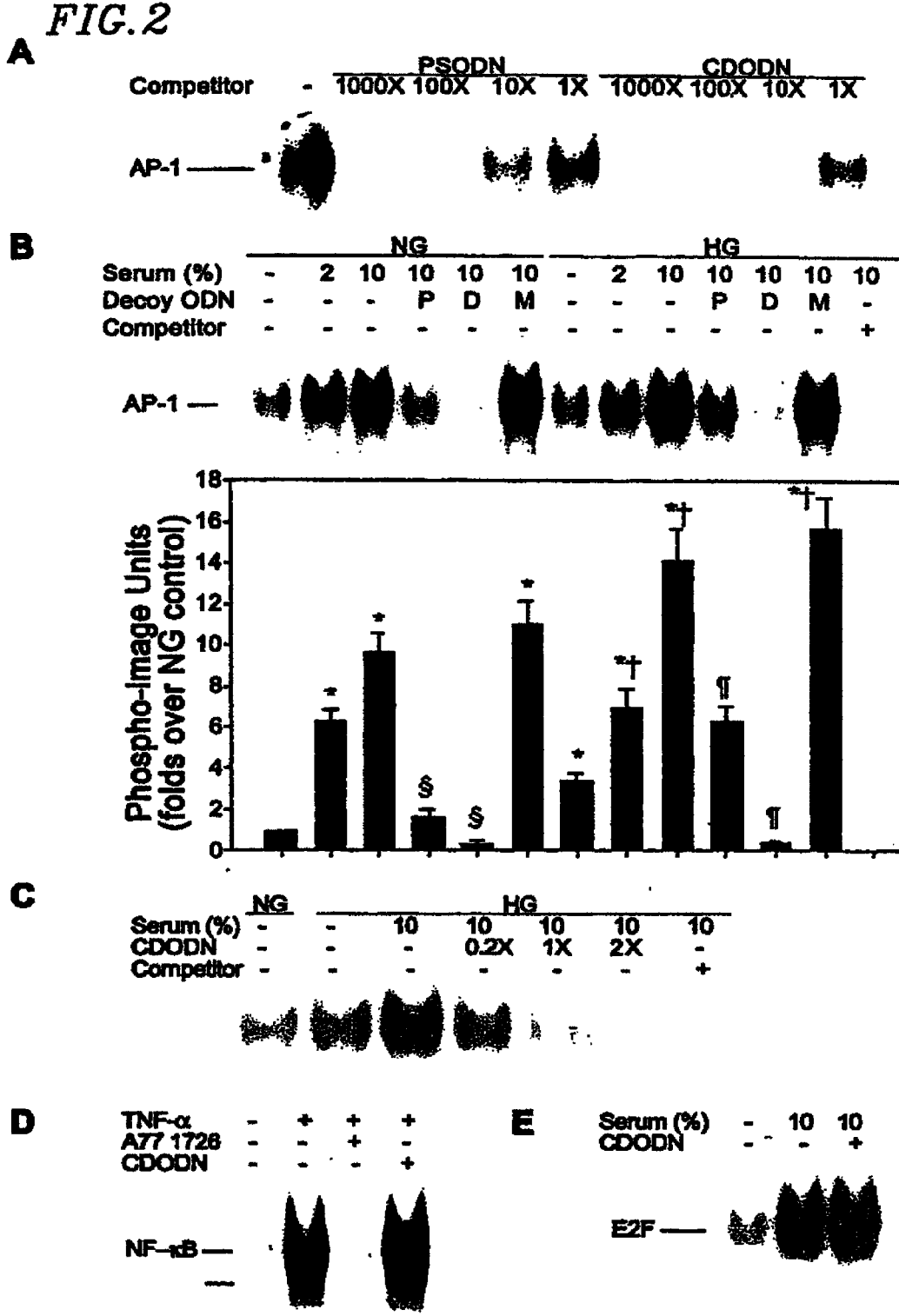
FIG. 2 shows effects of the CDODN on DNA binding activity of AP-1, NF-κB, and E2F. [A] Competition assay. AP-1 complexes were formed between labeled probe and the AP-1 protein in the presence of various concentrations of unlabeled oligonucleotides. [B] Typical example of a gel shift assay from VSMC transfected with the AP-1 decoy ODN. This experiment was repeated five times. NG; VSMC cultured with normal glucose (5.5 mmol/l D-glucose), HG; VSMC cultured with high glucose (25 mmol/l D-glucose), Decoy ODN; VSMC transfected with 100 nmol/l AP-1 decoy ODNs, P; PSODN, D; CDODN, M; mismatch AP-1 decoy ODN. Quantification of EMSA results expressed as the mean ±SEM of five independent experiments. $p<0.001$ compared to NG, $\dagger p<0.01$ compared to HG, $\S p<0.001$ compared to NG+10% serum, $\P p<0.01$ compared to HG+10% serum. [C] Dose-dependent effects of CDODN on a DNA binding assay. [D] Effects of CDODN on the TNFα-induced NF-κB DNA binding activity. [E] Effect of CDODN on serum-induced E2F DNA binding activity.

To demonstrate that the CDODN interact strongly enough with the AP-1 as decoys in a sequence-specific manner, an in vitro competition assay was performed. An increase in the non-labeled AP-1 decoy ODNs decreased the intensity of the retarded band, which corresponded to the complex formed by the AP-1 protein (FIG. 2A). A 1000-fold molar excess of the non-labeled PSODN as competitor almost completely competed for the AP-1 binding to labeled probe. When the CDODN was used as competitor in place of PSODN, a 100-fold molar excess of the non-labeled CDODN competitor completely competed for the AP-1 binding to labeled probe. Next, we transfected the CDODN and PSODN into cells under high glucose and serum stimulation conditions to investigate whether CDODN can specifically inhibit DNA-binding activity of AP-1. As expected, treatment with high glucose significantly increased AP-1 binding activity as compared to low glucose (FIG. 2B, $p<0.001$). Similarly, serum also increased. DNA binding activity of AP-1 in a dose-dependent manner ($p<0.001$). Transfection of both PSODN and CDODN significantly attenuated the AP-1 DNA binding activity induced by high glucose or serum ($p<0.01$), but CDODN exhibited higher inhibition of AP-1 binding activity ($p<0.001$).

Effect of AP-1 Decoy ODNs on Gene Expression in Smooth Muscle Cells

We used reporter gene constructs which contain the AP-1 binding site in the promoter region, to investigate the effect of AP-1 decoy ODN on promoter activity. To investigate the role of AP-1 binding site on up-regulation of cyclin A promoter activity by high glucose, we transfected a series of luciferase reporter gene plasmids containing various lengths of the human cyclin. A 5' flanking sequence into smooth muscle cells treated with high glucose. In these plasmids, only two plasmids (pCA-266/+205mt and pCA-133/−205mt) showed significantly decreased luciferase activity (FIG. 3A, $p<0.001$ compared with pCA-266/+205 or pCA-133/+205) and these reporter gene constructs were mutated ATF sites, which is responsible for AP-1 protein, from the cyclin A promoter. These data indicate that the AP-1 decoy ODN could down-regulate the promoter activity of cyclin A induced by high glucose in smooth muscle cells.

Next, we compared the effect of AP-1 decoy ODN on high glucose and serum induced-activity of luciferase reporter plasmids: pAP1(PMA)-TA-Luc and cyclin A promoter luciferase constructs (pCA-266/+205) containing the AP-1 binding site. As expected, co-transfection of luciferase reporters with both PSODN and CDODN markedly attenuated high glucose- and serum stimulated-luciferase gene expressions (FIGS. 3B and C, $p<0.01$). However, CDODN was more effective than PSODN ($p<0.01$ compared with PSODN). Therefore, we investigated the effect of AP-1 decoy ODN on endogenous expression of cell cycle-regulatory genes in vitro. For this purpose, gene expression of PCNA and cyclin A was measured by northern blotting. Both cyclin A and PCNA are required for cell cycle progression from the G1 phase to the S phase. As shown in FIG. 3D, both high glucose and serum stimulated the expression of PCNA and cyclin A mRNA in both human VSMC and rat aortic smooth muscle cells. Transfection of AP-1 decoy ODN, but not mismatched ODN, resulted in the attenuation of high glucose and serum induced-expression of these genes. Moreover, the inhibitory effect of CDODN on these gene expressions was stronger than PSODN in these stimulation conditions.

Effect of AP-1 Decoy ODNs on Inhibition of Smooth Muscle Cell Growth and Migration in Vitro Treatment with high glucose and serum stimulated growth of cultured primary human and rat VSMC compared to control (FIGS. 4A and 4B). Transfection of AP-1 decoy ODNs resulted in a significant inhibition of cell growth as compared to cells stimulated by high glucose or serum ($p<0.05$). Of note is that CDODN almost completely inhibited the cell growth ($p<0.01$). Similarly, the migration of VSMC was increased by both high glucose and serum as compared to control (FIGS. 4C and 4D, $p<0.05$), and while the migration stimulated by both high glucose and serum was significantly attenuated by treatment with AP-1 decoy ODNs ($p<0.01$), CDODN demonstrated the most potent inhibitory effects on the migration ($p<0.001$).

Effects of CDODN on Neointima Formation in Rat Balloon-Injured Carotid Artery

We tested the transfection efficiency of the HVJ-liposome method into rat carotid artery using fluorescent (FITC)-labeled AP-1 decoy ODN. Transfection of FITC-labeled ODN by HVJ-liposome method resulted in strong fluorescence (FIGS. 5A and B), readily detected in all layers of the artery. Thus, we chose the HVJ-liposome method to transfect AP-1 decoy ODN into rat carotid artery.

Using the HVJ-liposome method, we examined the effect of AP-1 decoy DEN on neointima formation in the rat carotid balloon-injury model. As shown in FIG. 5, vessels transfected with mismatched ODN exhibited neointima formation at 2 weeks after transfection similar to the untreated vessels. In contrast, a single administration of PSODN and CDODN resulted in a significant reduction in neointima formation ($p<0.001$). In agreement with in vitro data, the inhibitory effect of CDODN on neointima formation was more potent than PSODN ($p<0.0001$).

Next, we compared the effect of pre-treatment and post-treatment of AP-1 decoy DEN on inhibition of neointima formation in injured carotid arteries. As shown in FIG. 6, pre-treatment with AP-1 decoy ODN into rat carotid artery before balloon injury was more effective than post-treatment ($p<0.0001$ compared with balloon injured vessels, $p<0.01$ compared with post-treatment of CDODN) in the inhibition of neointima formation.

Effects of AP-1 Decoy ODNs on AP-1 DNA Binding Activity and Gene Expression in Vivo To confirm that AP-1 decoy ODN effectively blocked the AP-1 DNA binding activity in vivo, we performed the gel mobility shift assay using cells from injured arteries. As shown in FIG. 7A, AP-1 DNA binding activity was increased at 30 min after injury and was peaked at 3 h after injury. This activation was inhibited by treatment with CDODN. Pre-treatment with decoy ODN was more effective in attenuating the AP-1 activity than post-treatment.

The inhibitory effect of AP-1 decoy ODN on cell proliferation was confirmed by PCNA staining, which is widely used as a proliferation marker both in normal and disease states. As shown in FIG. 7B, there was no PCNA staining in uninjured arteries. Two weeks after injury, a marked increase in cells positive for PCNA staining was detected in neointima region and re-grown endothelial cells. In contrast, much fewer cells were positive for PCNA staining in vessels treated with AP-1 decoy ODNs, than in untransfected vessels.

Example 2

Effects of Novel E2F Decoy Oligodeoxynucleotides

Materials and Methods

Animals

Nine- to ten-week old male Sprague-Dawley (SD) rats weighing 280 to 320 g were used. All procedures were in accordance with institutional guidelines for animal research.

Cell Culture

Human VSMCs were isolated from thoracic aortas of heart transplant donors. The collection of this tissue was approved by the Ethics Committee of the institution. Rat VSMCs were harvested from thoracic aortas of adult male SD rats. VSMCs were cultured in DMEM (Gibco BRL, Grand Island, N.Y., USA) containing 20% FBS (Gibco BRL). VSMC purity was characterized by positive staining with smooth muscle specific α-actin monoclonal antibodies (Sigma, St. Louis, Mich., USA).

After reaching 80-90% confluence in 100-mm dishes, human VSMC were serum-starved for 24 h in serum free medium, and were subjected to either control normal glucose medium (DMEM containing 5.5 mmol/l D-glucose) or conditioned medium (DMEM containing 10% serum and 22 mmol/l D-glucose). Cells were then processed for nuclear protein extraction or RNA extraction as described below.

Construction of Dumbbell Type Decoy ODN

The sequences of dumbbell type and phosphorothioated double-stranded ODN against E2P binding site and mutated ODN used in this invention are as follows: CD-E2F (note; consensus sequences are underlined), 5'-GGATCCG TTTCGCGCTATTGCAAAAGCAATAGCGCGAAA C-3' (SEQ ID NO: 6); phosphorothioate E2P decoy (PS-E2F), 5'-ATsTTAAGTTTCGCGCCCTTTCTCAsAs-3' (SEQ ID NO: 7); mutated E2F decoy (M-E2F), 5'-GGATCCG TTTCGATTTATTGCAAAATCAATAAATCGAAAC-3' (SEQ ID NO: 8). CD-E2F was anticipated to form a stem-loop structure. The stem is formed by complementary sequences at both ends of each oligo. The 5' terminus of the stem has 6 bases of a single-stranded sequence of 5'-GGATCC-3' as enzyme site of BamHI. Two oligo molecules were joined by the complementary 6 base sequences at both 5' ends. ODN were annealed for 2 h, while the temperature descended from 80° C. to 25° C. One unit of T4 DNA ligase was added and incubated for 24 h at 16° C. to generate a covalently ligated Dumbbell type decoy molecule. CD-E2F consists of two loops and one stem containing two E2F consensus sequences (FIG. 8A).

Stability of CD-E2F

To test the stability of CD-E2F, 1 μg of each of the PS-E2F, non-ligated phosphodiester oligos and CD-E2F were incubated with either human serum, FBS, exonuclease III, or SI nuclease. All serums were used without heat inactivation to preserve DNase activity. Each serum was added to oligos to 50% in a 100 μl reaction volume and incubated for 24 h at 37° C. Exonuclease III (Takara, Otsu, Japan) at 160 units/μg oligos was added to oligos and incubated for 2 h at 37° C. SI nuclease (Takara) at 10 units/μg oligos was added to oligos and incubated for 30 min at 25° C. The oligos were then extracted with phenol and chloroform and were examined on a 15% denaturing polyacrylamide gel.

In Vitro Gene Transfer

Cells were fed with fresh culture medium 1 day prior to adding decoy and washed twice with Opti-MEM (Gibco BRL) prior to each experiment. Cells were transfected with 100 nM of decoy ODNs combined with Lipofectin™ (molar ratio; DNA:lipid=1:3) (Gibco BRL). The mixture of decoy ODN:Lipofectin was added to the cells dropwise according to the manufacturer's instructions. The cells were incubated at 37 for for 5 h. Then, after changing to fresh medium with 10% FBS, the cells were incubated in a $CO_2$ incubator.

Effect of Decoy ODN on VSMC Growth

VSMC were seeded onto 96-well tissue culture plates. At 30% confluence, SMC were rendered quiescent by incubation for 24 hours in defined serum-free medium. Then, Lipofectin:decoy ODN (containing 100 nM ODN) was added to the wells. The cells were incubated at 37° C. for 5 h. After 2-3 days, an index of cell proliferation was determined with the use of a WST cell counting kit (Wako, Osaka, Japan).

Electrophoretic Mobility Shift Assay (EMSA)

Nuclear extracts were prepared from VSMC as described in Ahn J D et al 2001 supra. In brief, the DNA probes such as those for E2F and mutated ODN were labeled as primers using [$\gamma$-$^{32}$P]ATP and T4 polynucleotide kinase. After end labeling, $^{32}$P-labeled ODN were purified with a NAP-5 column. The protein-DNA binding reaction was performed at room temperature for 20 min in a volume of 20 μl. The reaction mixture contained 6 μg of nuclear extract, 100 μg/ml poly dI:dC, 10 mmol/l Tris/HCl (pH 7.5), 50 mmol/l NaCl, 0.5 mmol/l EDTA, 0.5 mmol/l DTT 1 mmol/l $MgCl_2$, 4% glycerol and 60,000 cpm $^{32}$P-labeled primer DNA. After incubation, the samples were loaded onto 4% native polyacrylamide gels in 0.5× Tris-borate-EDTA buffer and were run at 150 V for 2 h. The gels were dried and visualized by autoradiography. For competition studies, the experimental conditions were identical, except that the appropriate competitor ODN was added at 50- to 100-fold molar excess to the reaction mixture before the addition of nuclear extract.

Northern Blot Analysis

Gene expression of PCNA and cyclin A was measured by Northern blot. 10 μg of total RNA was applied to 1% formaldehyde-agarose gel, and transferred to a nylon membrane. The nylon membrane was hybridized in Express Hyb™ solution at 65° C. for 2 h with radiolabeled PCNA cDNA probe or cyclin A cDNA probe (donated by Dr Young-Chae Chang, Dankook University Medical School, Korea), and washed according to the manufacturer's instructions. The membrane was exposed to X-ray film for 24-48 h, and the mRNA expression was quantified with densitometric analysis. Loading differences were normalized using a 18s rRNA cDNA probe.

Preparation of Hemagglutinating Virus of Japan (HVJ)-Liposomes

HVJ-liposomes were prepared as described in Ahn J D et al 2001 supra. Briefly, cholesterol, dioleoyl-phosphatidylethanolamine, phosphatidylcholine, sphingomyelin and phosphatidylserine were mixed in a molar ratio of 50:13.3:13.3:13.3:10. The lipid mixture was deposited on the sides of a flask by removal of chloroform. Dried lipid was hydrated in 200 μl balanced salt solution (BSS; 137 mmol/l NaCl, 5.4 mmol/l KCl, 10 mmol/l Tris-HCl, pH 7.6) containing ODN. Liposomes were prepared by shaking and filtration. Purified HVJ (Z strain) was inactivated by UV irradiation for 3 min just before use. The liposome suspension was mixed with HVJ in a total volume of 2 ml BSS. The mixture was incubated at 4° C. for 5 min and then for 30 min with gentle shaking at 37° C. Free HVJ was removed from the HVJ-liposomes by sucrose density gradient centrifugation. The top layer of the sucrose gradient was collected for use.

Balloon Injury and in Vivo Gene Transfer

A 2 French Fogarty catheter was used to induce vascular injury in male SD rats. These rats were anesthetized with pentobarbital, and the left common carotid artery was surgically exposed. A cannula was introduced into the common carotid artery via the external carotid artery. In vivo gene transfer was performed after inducing vascular injury of the common carotid artery by inflating an inserted balloon catheter three times. The injured segment was transiently isolated by temporary ligatures. After balloon injury, 20 μl of HVJ-liposomes complex containing either CD-E2F, M-E2F, FITC-labeled PS-E2F or HVJ-liposome only was incubated within the lumen for 10 min at room temperature. After a 10-min incubation, the infusion cannula was removed. After the transfection, blood flow the common carotid artery was restored by release of the ligatures, and the wound was then closed. No adverse neurological or vascular effects were observed in any animal that underwent this procedure.

Luciferase Assay

An E2F luciferase construct was kindly provided by Dr. Youngchae Jang (Dankook University, Chunan, Korea). To analyze the luciferase expression, the cells were washed twice with PBS and were lysed with 200 μl of 1× Reporter lysis buffer (Promega, Madison, Wis., USA). Fifty microliters of each lysate were examined for luciferase activity.

Histological Analysis

At 2 wk after transfection, rats were sacrificed and vessels were perfusion fixed with 4% paraformaldehyde. Neointima size was quantified by morphometry by individuals who were blinded to the identity of the samples. Intimal and medial areas were measured on a digitizing system (model INTUOS 6x8, Wacom, Vancouver, Wash., USA). In case of FITC-labeled E2F decoy ODN transfection, the vessels were harvested at 3 d after transfection and perfusion fixed with 4% paraformaldehyde. Sections were examined by fluorescence microscopy. For immunohistochemisty, sections were incubated with rabbit anti-proliferating cell nuclear antigen antibody (1:200 dilution, SantaCruz, Santa Cruz, Calif., USA) and processed for immunohistochemistry in a standard manner.

Statistical Analysis

Results are expressed as mean±SEM. Analysis of variance with subsequent Duncan's test was used to determine the significance of differences in multiple comparisons. $P<0.05$ was considered statistically significant. All experiments were carried out at least three times.

Results

Stability of CD-E2F

To investigate the stability of newly synthesized CD-E2F, we initially examined molecular stability in the presence of nucleases (FIG. 8B). CD-E2F was, as expected, resistant to exonuclease III and was observed as a major band on gel electrophoresis. In contrast to CD-E2F, both PS-E2F and annealed decoy were completely degraded after 2 h of incubation with exonuclease III. To confirm the stem loop structure of CD-E2F, we further examined the molecular characteristics of CD-E2F using S1 nuclease. The decoys were incubated with S1 nuclease, which digests single-stranded regions in DNA molecules. Both the stem regions of CD-E2F (74 bases) and PS-E2F (50 bases) were found to be protected from S1 nuclease, but not that of the annealed type decoy (FIG. 8B).

It has been reported that exonuclease activity constitutes most of the nuclease activity in the cytoplasm and serum. Therefore, we tested the stability of the decoys by incubation with serums that were not heat-inactivated. Decoys were treated with 50% non-inactivated human serum, FBS, or calf serum for 24 h. Both PS-E2F and annealed type decoy were significantly hydrolyzed after 24 h of incubation in the presence of each serum. CD-E2F, however, remained largely intact, after 24 h of incubation with these different serums, exhibiting improved stability compared with both PS-E2F and annealed type decoy (FIG. 8B).

Specific Binding of the E2F to CD-E2F with the E2F Target Site

To test the sequence specificity of CD-E2F, an in vitro competition assay was performed. An increase in the non-labeled E2F decoys decreased the intensity of the retarded band, which corresponded to the complex formed by the E2F protein (FIG. 9A). A 1000-fold molar excess of the non-labeled PS-E2F as competitor completely competed for the E2F binding to labeled probe. On the other hand, when the CD-E2F was used as competitor in place of PS-E2F, only a 100-fold molar excess of the non-labeled CD-E2F competitor was needed to completely compete for the E2F binding to labeled probe. Next, we transfected decoys into cells to investigate whether decoys can specifically inhibit DNA-binding activity of E2F. As expected, culturing in conditioned media containing high glucose and serum significantly increased E2F binding activity as compared to culturing in control media (FIG. 9B, $p<0.01$). Transfection of PS-E2F and CD-E2F significantly attenuated the E2F DNA binding activity induced by high glucose and serum ($p<0.01$). However, the increase in E2F DNA binding activity induced by high glucose and serum was inhibited strongly by CD-E2F as compared to the PS-E2F ($p<0.05$).

Effect of E2F Decoy on Cyclin Promoter Activity in Smooth Muscle Cells

We used reporter gene constructs, which contain the E2F binding site in the promoter region, to investigate the effect of E2F decoy on promoter activity. To investigate the role of E2F binding site on up-regulation of cyclin A promoter activity by high glucose, we transfected a series of luciferase reporter gene plasmids containing various lengths of the human cyclin. A 5' flanking sequence into smooth muscle cells treated with high glucose. In these plasmids, only two plasmids (pCA-133/+205 and pCA-133/−2) showed significantly decreased luciferase activity (FIG. 10A) and the activity of pCA-133/−2 constructs, which we deleted two E2F binding sites from the cyclin A promoter, was lowest. These data indicate that the E2F site mediates up-regulation of cyclin A promoter activity by high glucose in VSMC. Next, we investigated the inhibitory effect of E2F decoy on promoter activity of reporter gene plasmids pCA-266/+205 and [E2F]×4-Luc, which contains four E2F binding sites in promoter region. As expected, co-transfection of E2F decoy markedly attenuated up-regulated luciferase gene expression by high glucose and serum (FIGS. 10B and C, $p<0.01$). Also, the CD-E2F was more effective than PS-E2F ($p<0.05$) and the M-E2F did not abolish the increase in luciferase activity.

Effect of E2F Decoys on Expression of Cell Cycle-Regulatory Genes in VSMC

We assessed the effect of E2F decoy on expression of the endogenous cell cycle-regulatory gene. As shown in FIG. 11, high glucose and serum stimulated the expression of cyclin A and PCNA gene in both human VSMC and Rat ASMC ($p<0.01$). Transfection of E2F decoy, but not M-E2F, resulted in the attenuation of gene expression of PCNA and cyclin A ($p<0.01$). 18S rRNA expression was not affected by the transfection of E2F decoy. The inhibitory effect of CD-E2F on expression of these genes was stronger than PS-E2F under these stimulation conditions ($p<0.05$).

Effect of E2F Decoy on Inhibition of VSMC Growth in Vitro

Since common characteristic of vascular responses to balloon injury is proliferation of VSMC, E2F decoys were tested for their ability to inhibit smooth muscle cell growth. Treatment with high glucose and serum stimulated growth of cultured primary human and rat VSMC compared to control (FIGS. 12A and B), as assessed by WST cell counting kits. Transfection of E2F decoy resulted in a significant inhibition of cell growth as compared to cells stimulated by high glucose or serum ($p<0.01$). CD-E2F almost completely inhibited cell growth. ($p<0.05$ compared with PS-E2F).

Effects of CD-E2F on Balloon Injured Rat Carotid Artery

We tested the efficiency of transfecting the E2F decoy into rat carotid artery using the HVJ-liposome method. Transfection of a FITC-labeled E2F decoy using the HVJ-liposome method resulted in a strong fluorescence (FIG. 13B), readily detected in all layers of the artery. Thus, we chose to employ the HVJ-liposome method to transfect the E2F decoy into rat carotid artery for the remainder of the experiments.

We examined the effect of an in vivo antigene strategy using the E2F decoy in the rat carotid balloon injury model. As shown in FIG. 13, vessels transfected with M-E2F exhibited neointima formation at 2 weeks after transfection similar to the untreated vessels. In contrast, a single administration of PS-E2F and CD-E2F resulted in a significant reduction in neointima formation ($p<0.001$). In agreement with in vitro data, the inhibitory effect of CD-E2F on neointima formation was more potent than PS-E2F ($p<0.05$). Decoy treatment did not alter the medial area. The reduction in neointima formation was limited to transfected regions.

The gene for PCNA was shown to be E2F dependent and was originally defined as a nuclear protein whose appearance correlated with the proliferative state of the cell. We thus explored the effect of balloon injury on PCNA expression and whether treatment with E2F decoy inhibits PCNA expression. As shown in FIG. 14, there was no PCNA staring in control, uninjured arteries. Two weeks after injury there was a marked increase of PCNA staining positive cells in neointima region and regrowing endothelial cells. In contrast, the number of PCNA staining positive cells in E2F decoy treated vessels was much lower than in untreated vessels.

Example 3

Effects of Novel NF-κB Decoy Oligodeoxynucleotides

Construction of Dumbbell Type Decoy ODN

The sequences of dumbbell type and phosphorothioated double-stranded ODN against NFκB binding site and mutated ODN used in this invention are as follows: CD-NF (note; consensus sequences are underlined), 5'-GGATCCG GGGATTTCTATTGCAAAAGCAATAGCGCGAAAC-3' (SEQ ID NO: 15); phosphorothioate NFκB decoy (PS-NF), 5'-ATsTTAAGGGGATTTCCCTTTCTCAsAs-3' (SEQ ID NO: 16); mutated E2F decoy (M-NF), 5'-GGATCCG GGGATATTTATTGCAAAAGCAATAAATCGAAAC-3' (SEQ ID NO: 17). CD-NF was anticipated to form a stem-loop structure. The stem is formed by complementary sequences at both ends of each oligo. The 5' terminus of the stem has 6 bases of a single-stranded sequence of 5'-GGATCC-3' as enzyme site of BamHI. Two oligo molecules were joined by the complementary 6 base sequences at both 5' ends. ODN were annealed for 2 h, while the temperature descended from 80° C. to 25° C. One unit of T4 DNA ligase was added and incubated for 24 h at 16° C. to generate a covalently ligated Dumbbell type decoy molecule. CD-NF consists of two loops and one stem containing two NFκB consensus sequences.

Synthesis of an NF-κB Decoy (Decoy Oligonucleotide)

On a DNA synthesizer, an NF-κB decoy oligonucleotide and a scrambled decoy oligonucleotide (an oligonucleotide having the same base composition as the NF-κB decoy oligonucleotide but a randomized sequence), the nucleotide sequences of which are shown below, were respectively synthesized from S-oligonucleotides. Those nucleotides were heated at 80° C. for 30 minutes and then allowed to cool to room temperature over 2 hours to provide double-stranded DNAs.

```
NF-κB decoy oligonucleotide
CCTTGAAGGGATTTCCCTCC     (SEQ ID No. 9)

GGAACTTCCCTAAAGGGAGG     (SEQ ID No. 18)

Scrambled decoy oligonucleotide
TTGCCGTACCTGACTTAGCC     (SEQ ID No. 19)

AACGGCATGGACTGAATCGG     (SEQ ID No. 20)
```

Stability of CD-NF

To test the stability of CD-NF, 1 μg of each of the PS-NF, non-ligated phosphodiester oligos and CD-NF were incubated with either human serum, FBS, exonuclease III, or S1 nuclease. All serums were used without heat inactivation to preserve DNase activity. Each serum was added to oligos to 50% In a 100 μl reaction volume and incubated, for 24 h at 37° C. Exonuclease III (Takara, Otsu, Japan) at 160 units/μg oligos was added to oligos and incubated for 2 h at 37'C. S1 nuclease (Takara) at 10 units/μg oligos was added to oligos and incubated for 30 min at 25° C. The oligos were then extracted with phenol and chloroform and were examined on a 15% denaturing polyacrylamide gel.

In Vitro Gene Transfer

Cells were fed with fresh culture medium 1 day prior to adding decoy and washed twice with Opti-MEM (Gibco BRL) prior to each experiment. Cells were transfected with 5 μM of decoy ODNs combined with Lipofectin™ (molar ratio; DNA:lipid=1:3) (Gibco BRL). The mixture of decoy ODN: Lipofectin was added to the cells dropwise according to the manufacturer's instruction. The cells were incubated at 37° C. for 5 h. Then, after changing to fresh medium with 10% FBS, the cells were incubated in a $CO_2$ incubator.

Preparation of Hemagglutinating Virus of Japan (HVJ)-Liposomes of CD-NF.

HVJ-liposomes were prepared as described in Ahn J D et al 2001 supra. Briefly, cholesterol, dioleoyl-phosphatidylethanolamine, phosphatidylcholine, sphingomyelin and phosphatidylserine were mixed in a molar ratio of 50:13.3:13.3: 13.3:10. The lipid mixture was deposited on the sides of a flask by removal of chloroform. Dried lipid was hydrated in 200 μl balanced salt solution (BSS; 137 mmol/1 NaCl, 5.4 mmol/1 KCl, 10 mmol/1 Tris-HCl, pH 7.6) containing ODN. Liposomes were prepared by shaking and filtration. Purified HVJ (Z strain) was inactivated by UV irradiation for 3 min lust before use. The liposome suspension was mixed with HVJ in a total volume of 2 ml BSS. The mixture was incubated at 4° C. for 5 min and then for 30 min with gentle shaking at 37° C. Free HVJ was removed from the HVJ-liposomes by sucrose density gradient centrifugation. The top layer of the sucrose gradient was collected for use.

Production of Liposomal Preparations of Normal NFκB Decoy

Phosphatidylserine, phosphatidylcholine, and cholesterol, provided in a weight ratio of 1:4.8:2 (a total of 10 mg), were dissolved in tetrahydrofuran. Using a rotary evaporator, the tetrahydrofuran was removed from the lipid solution to leave the lipid in the form of a film adherent to the flask wall. To this was added 200 ml of saline (BSS; 139 mM NaCl, 5.4 mM KCl, 10 mM Tris-HCl, pH7.6) containing the NF-κB decoy oligonucleotide (0.7 mg) prepared in Example 1 and the mixture was stirred and sonicated under the usual conditions to provide a suspension of liposomes containing the NF-κB decoy oligonucleotide. This suspension of liposome vesicles (0.5 ml, lipid content 10 mg) was mixed with purifyed Sendai virus (Z strain, 10000 hemagglutinating units) exposed to UV radiation (110 erg/mm2/sec) 3 minutes before use and the mixture was made up to 4 ml with BSS. This mixture was held at 4° C. for 5 minutes and, then subjected to gentle shaking at 37° C. for 30 minutes. After the Sendai virus not bound to the liposomes was removed by sucrose density gradient centrifugation, the uppermost layer was separated and its concentration was adjusted with BSS to provide a liposomal preparation containing 8 μM NF-κB decoy oligonucleotide as entrapped. A liposomal preparation was similarly produced using the scrambled decoy oligonucleotide of Example 1 in lieu of the NF-κB decoy oligonucleotide.

Reperfusion Model Experiment (1) Method

After 9-10-week-old SD rats were anesthetized with pentobarbital sodium, a cannula was inserted into the left carotid artery adjacent to the airway and indwelled near the aortic valve of the heart (close to the ostium of the coronary artery). In addition, the trachea was cannulated and the animal was placed on supportive respiration by connecting the tracheal cannula to an artificial respirator. Thereafter, a left intercostal incision was made and the left descending anterior branch of the rat heart was ligated to produce ischemia. After 30 minutes, the ligating suture was cut to start reperfusion. Immediately thereafter, 1.5 ml/rat of the liposomally entrapped CD-NF, PS-NF, M-NF, NF-κB decoy nucleotide or scrambled decoy nucleotide prepared above was administered via the cannula indwelled close to the ostium of the coronary artery. After the chest was closed, the trachea was also sutured and the animal was kept alive. After 24 hours, the rat was reanesthetized and the heart was enucleated and washed with saline. The ventricle of the rat heart was sliced into six sections which were stained with tetrazolium chloride (TTC). The six sections were respectively photographed and subjected to image analysis. The infarcted area was calculated by means of the following equation.

Infarction rate (%)=the sum of infarct areas of 6 sections/the sum of areas of 6 sections×100

Statistical analysis was made by multiple comparison (ANOVA).

(2) Results

In the untreated control group, M-NF and the scrambled decoy treatment group, myocardial infarcts are found in approximately equal degrees. In the group given the CD-NF, the PS-NF and the NF-κB decoy nucleotide, the infarct is suppressed to significant degree from the untreated group, M-NF and the scrambled decoy group. Among these positive groups, the group given the CD-NF shows significantly greater suppression than in normal decoy or PS-NF.

A similar inhibitory effect was found when the liposomes were administered immediately before induction of infarction.

Inhibition of Cancer Metastasis (1) Method

To 7-week-old female mice of the C57BL/6 strain, 1×104 marine reticulum cell sarcoma M5076 cells were administered intravenously and 24 hours later 0.2 ml (6 nmoles) of each of liposomally entrapped. CD-NF, PS-NF, M-NF, NF-κB decoy nucleotide or scrambled decoy nucleotide prepared above prepared in the same manner as above was administered intravenously. A control group received 0.2 ml of saline in the same manner. On day 14 after intravenous administration of M5076, the animal was autopsied and the number of tumor nodules on the surface of the liver was counted under the stereoscopic microscope. Each group consisted of 10 mice. For statistical analyses, Kruskal-Wallis test and Dunnett's multiple comparison were used.

(2) Results

CD-NF, PS-NF and NF-κB decoy treatment groups showed a significant effects in suppressing the tumor size than in the groups treated with M-NF or the control group. Among these positive groups, the group given the CD-NF shows significantly greater suppression in tumor size than in normal decoy or PS-NF.

Inhibition of Cachexia (1) Method

Using 7-week-old male BALB/c mice, a 2 mm cubic tumor mass of murine colon cancer line Colon 26 was transplanted subdermally. Beginning day 7 after transplantation, 0.2 ml (6 nmoles) of liposomally entrapped CD-NF, PS-NF, M-NF, NF-κB decoy nucleotide or scrambled decoy nucleotide prepared above was administered into the tumor mass and the body weight and tumor weight were serially determined. The animal was autopsied on day 13 and the epididymal fat and gastrocnemius muscle were isolated and weighed. Furthermore, 5 the wet carcass weight exclusive of all the remaining organs and tumor was determined. The tumor weight was calculated from the major and minor diameters of each tumor mass by means of the following equation.

Tumor weight (mg)=major diameter×minor diameter2/2

Each group consisted of 10 mice. Statistical analyses were made by ANOVA in one-way layout and Dunnett's multiple comparison.

(2) Results

In the tumor-bearing group, growth of the tumor resulted in significant decreases in body weight, epididymal fat weight, gastrocnemius muscle weight, and wet carcass weight. In the CD-NF, PS-NF and NF-κB decoy groups, improvements are obtained. This improvement is significantly higher in the CD-NF group than in PS-NF or NF-κB group. However, no improvement is found in M-NF and the scrambled decoy groups. There is no definite effect on tumor weight in M-NF or the scrambled decoy group.

The descriptions of the foregoing embodiments of the invention have been presented for purpose of illustration and description. They are not intended to be exhaustive or to limit the invention to the precise form disclosed, and obviously many modifications and variations are possible in light of the above teachings. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto. All references cited herein are hereby incorporated by reference.

INDUSTRIAL APPLICABILITY

The present invention provides a circular dumbbell oligodeoxynucleotide (CDODN) comprising two loop structures and a stem structure, wherein the stem structure comprises a nucleotide sequence capable of binding the DNA-binding domain of a transcriptional factor. The present invention further provides a pharmaceutical composition comprising said CDODN. The pharmaceutical composition can be used for treating and/or preventing a disease or disorder related to such a transcriptional factor. The present invention also provides a method for treating and/or preventing a disease or disorder related to such a transcriptional factor, comprising administering to the subject a therapeutically effective amount of a CDODN comprising two loop structures and a stem structure, wherein the stem structure comprises a nucleotide sequence capable of binding the DNA-binding domain of the transcriptional factor.

Further, the present invention provides methods and compositions for the treatment of restenosis following angioplasty, by inhibiting the trans-activation ability of the transcription factor AP-1. These compositions and methods are useful in the treatment of vascular disorders. The present invention also provides novel circular dumbbell oligodeoxynucleotide decoys (CDODNs) to the transcription factors AP-1 and E2F, which are useful in the treatment of AP-1 and E2F-associated disorders and in elucidating the cellular role of these transcription factors.

---

The invention claimed is:

1. A method for reducing reperfusion injury in a mammal suffering from said reperfusion injury, the method comprising administering into regional blood vessels in a region of the mammal affected by said reperfusion injury a therapeutically effective amount of a circular dumbbell oligodeoxynucleotide (CDODN) comprising two loop structures and a stem structure, and reducing said reperfusion injury, wherein the stem structure comprises a nucleotide sequence capable of binding the DNA-binding domain of NF-κB transcriptional factor,
   wherein the CDODN comprises two identical stem loop structures covalently linked by enzymatic ligation, wherein each of the identical stem loop structures comprises SEQ ID NO: 15, and wherein the therapeutically effective amount of the CDODN is administered in a Hemagglutinating Virus of Japan (HVJ) liposome composition.

2. The method according to claim 1, wherein the regional blood vessels are arteries.

3. The method according to claim 1, wherein the mammal is a human.

4. The method according to claim 1, wherein said region of the mammal affected by said reperfusion injury is located on heart of said mammal and said reducing reperfusion injury results in suppression of myocardial infarcts caused by said reperfusion injury.

* * * * *

SEQUENCE LISTING

```
<160> NUMBER OF SEQ ID NOS: 26

<210> SEQ ID NO 1
<211> LENGTH: 19
<212> TYPE: DNA
<213> ORGANISM: Artificial Sequence
<220> FEATURE:
<223> OTHER INFORMATION: synthetic AP-1 decoy

<400> SEQUENCE: 1
agcttgtgag tcagaagct                                              19

<210> SEQ ID NO 2
<211> LENGTH: 25
<212> TYPE: DNA
<213> ORGANISM: Artificial Sequence
<220> FEATURE:
<223> OTHER INFORMATION: synthetic E2F decoy

<400> SEQUENCE: 2
atttaagttt cgcgcccttt ctcaa                                       25
```

```
<210> SEQ ID NO 3
<211> LENGTH: 41
<212> TYPE: DNA
<213> ORGANISM: Artificial Sequence
<220> FEATURE:
<223> OTHER INFORMATION: synthetic CD-AP1

<400> SEQUENCE: 3
ggatccatga ctcagaagac gacacacgtc ttctgagtca t            41

<210> SEQ ID NO 4
<211> LENGTH: 19
<212> TYPE: DNA
<213> ORGANISM: Artificial Sequence
<220> FEATURE:
<223> OTHER INFORMATION: synthetic PSODN

<400> SEQUENCE: 4
agcttgtgac tcagaagct                                      19

<210> SEQ ID NO 5
<211> LENGTH: 40
<212> TYPE: DNA
<213> ORGANISM: Artificial Sequence
<220> FEATURE:
<223> OTHER INFORMATION: synthetic MODN

<400> SEQUENCE: 5
ggatccaaat ctcagaagac gacacacgtc ttctgagatt              40

<210> SEQ ID NO 6
<211> LENGTH: 80
<212> TYPE: DNA
<213> ORGANISM: Artificial Sequence
<220> FEATURE:
<223> OTHER INFORMATION: synthetic CD-E2F

<400> SEQUENCE: 6
ggatccgttt cgcgctattg caaaagcaat agcgcgaaac ggatccgttt cgcgctattg    60
caaaagcaat agcgcgaaac                                     80

<210> SEQ ID NO 7
<211> LENGTH: 25
<212> TYPE: DNA
<213> ORGANISM: Artificial Sequence
<220> FEATURE:
<223> OTHER INFORMATION: synthetic PS-E2F

<400> SEQUENCE: 7
atttaagttt cgcgcccttt ctcaa                              25

<210> SEQ ID NO 8
<211> LENGTH: 80
<212> TYPE: DNA
<213> ORGANISM: Artificial Sequence
<220> FEATURE:
<223> OTHER INFORMATION: synthetic M-E2F

<400> SEQUENCE: 8
ggatccgttt cgatttattg caaaagcaat aaatcgaaac ggatccgttt cgatttattg    60
caaaagcaat aaatcgaaac                                     80

<210> SEQ ID NO 9
<211> LENGTH: 20
```

```
<212> TYPE: DNA
<213> ORGANISM: Artificial Sequence
<220> FEATURE:
<223> OTHER INFORMATION: synthetic NF-kappaB decoy

<400> SEQUENCE: 9
ccttgaaggg atttccctcc                                           20

<210> SEQ ID NO 10
<211> LENGTH: 28
<212> TYPE: DNA
<213> ORGANISM: Artificial Sequence
<220> FEATURE:
<223> OTHER INFORMATION: synthetic STAT-1 decoy

<400> SEQUENCE: 10
gatctaggga tttccgggaa atgaagct                                  28

<210> SEQ ID NO 11
<211> LENGTH: 16
<212> TYPE: DNA
<213> ORGANISM: Artificial Sequence
<220> FEATURE:
<223> OTHER INFORMATION: synthetic GATA-3 decoy

<400> SEQUENCE: 11
agcttgagat agagct                                               16

<210> SEQ ID NO 12
<211> LENGTH: 28
<212> TYPE: DNA
<213> ORGANISM: Artificial Sequence
<220> FEATURE:
<223> OTHER INFORMATION: synthetic STAT-6 decoy

<400> SEQUENCE: 12
gatcaagacc ttttcccaag aaatctat                                  28

<210> SEQ ID NO 13
<211> LENGTH: 19
<212> TYPE: DNA
<213> ORGANISM: Artificial Sequence
<220> FEATURE:
<223> OTHER INFORMATION: synthetic AP-1 decoy

<400> SEQUENCE: 13
agcttgtgag tcagaagct                                            19

<210> SEQ ID NO 14
<211> LENGTH: 20
<212> TYPE: DNA
<213> ORGANISM: Artificial Sequence
<220> FEATURE:
<223> OTHER INFORMATION: synthetic Ets decoy

<400> SEQUENCE: 14
aattcaccgg aagtattcga                                           20

<210> SEQ ID NO 15
<211> LENGTH: 40
<212> TYPE: DNA
<213> ORGANISM: Artificial Sequence
<220> FEATURE:
<223> OTHER INFORMATION: synthetic CD-NF

<400> SEQUENCE: 15
ggatccgggg atttctattg caaaagcaat agcgcgaaac                     40
```

-continued

```
<210> SEQ ID NO 16
<211> LENGTH: 25
<212> TYPE: DNA
<213> ORGANISM: Artificial Sequence
<220> FEATURE:
<223> OTHER INFORMATION: synthetic PS-NF

<400> SEQUENCE: 16
atttaagggg atttcccttt ctcaa                                               25

<210> SEQ ID NO 17
<211> LENGTH: 40
<212> TYPE: DNA
<213> ORGANISM: Artificial Sequence
<220> FEATURE:
<223> OTHER INFORMATION: synthetic M-NF

<400> SEQUENCE: 17
ggatccgggg atatttattg caaaagcaat aaatcgaaac                               40

<210> SEQ ID NO 18
<211> LENGTH: 20
<212> TYPE: DNA
<213> ORGANISM: Artificial Sequence
<220> FEATURE:
<223> OTHER INFORMATION: synthetic NF-kappaB decoy reverse

<400> SEQUENCE: 18
ggaacttccc taagggagg                                                      20

<210> SEQ ID NO 19
<211> LENGTH: 20
<212> TYPE: DNA
<213> ORGANISM: Artificial Sequence
<220> FEATURE:
<223> OTHER INFORMATION: synthetic Scrambled decoy

<400> SEQUENCE: 19
ttgccgtacc tgacttagcc                                                     20

<210> SEQ ID NO 20
<211> LENGTH: 20
<212> TYPE: DNA
<213> ORGANISM: Artificial Sequence
<220> FEATURE:
<223> OTHER INFORMATION: synthetic Scrambled decoy reverse

<400> SEQUENCE: 20
aacggcatgg actgaatcgg                                                     20

<210> SEQ ID NO 21
<211> LENGTH: 40
<212> TYPE: DNA
<213> ORGANISM: Artificial Sequence
<220> FEATURE:
<223> OTHER INFORMATION: synthetic CD-AP1

<400> SEQUENCE: 21
gaattcatga ctcagaagac gaaaacgtct tctgagtcat                               40

<210> SEQ ID NO 22
<211> LENGTH: 80
<212> TYPE: DNA
<213> ORGANISM: Artificial Sequence
<220> FEATURE:
<223> OTHER INFORMATION: synthetic mismatched CD-AP1
```

```
<400> SEQUENCE: 22
gaattcaaat ctcagaagac gaaaacgtct tctgagattt gaattcaaat ctcagaagac     60
gaaaacgtct tctgagattt                                                 80

<210> SEQ ID NO 23
<211> LENGTH: 19
<212> TYPE: DNA
<213> ORGANISM: Artificial Sequence
<220> FEATURE:
<223> OTHER INFORMATION: synthetic PSODN

<400> SEQUENCE: 23
agcttctgag tcacaagct                                                  19

<210> SEQ ID NO 24
<211> LENGTH: 25
<212> TYPE: DNA
<213> ORGANISM: Artificial Sequence
<220> FEATURE:
<223> OTHER INFORMATION: synthetic PS-E2F

<400> SEQUENCE: 24
ttgagaaagg gcgcgaaact taaat                                           25

<210> SEQ ID NO 25
<211> LENGTH: 80
<212> TYPE: DNA
<213> ORGANISM: Artificial Sequence
<220> FEATURE:
<223> OTHER INFORMATION: synthetic CD-AP1

<400> SEQUENCE: 25
gaattcatga ctcagaagac gaaaacgtct tctgagtcat gaattcatga ctcagaagac     60
gaaaacgtct tctgagtcat                                                 80

<210> SEQ ID NO 26
<211> LENGTH: 40
<212> TYPE: DNA
<213> ORGANISM: Artificial Sequence
<220> FEATURE:
<223> OTHER INFORMATION: synthetic CD-E2F

<400> SEQUENCE: 26
ggatccgttt cgcgctattg caaaagcaat agcgcgaaac                           40
```